United States Patent
Youssef et al.

(10) Patent No.: US 9,357,948 B2
(45) Date of Patent: Jun. 7, 2016

(54) METHOD AND SYSTEM FOR DETERMINING THE VALUES OF PARAMETERS REPRESENTATIVE OF A MOVEMENT OF AT LEAST TWO LIMBS OF AN ENTITY REPRESENTED IN THE FORM OF AN ARTICULATED LINE

(75) Inventors: Joe Youssef, Grenoble (FR); Christelle Godin, Brignoud (FR); Suzanne Lesecq, Froges (FR)

(73) Assignees: COMMISSARIAT A L'ENERGIE ATOMIQUE ET AUX ENERGIES ALTERNATIVES, Paris (FR); MOVEA, Grenoble (FR)

( * ) Notice: Subject to any disclaimer, the term of this patent is extended or adjusted under 35 U.S.C. 154(b) by 251 days.

(21) Appl. No.: 13/991,015

(22) PCT Filed: Dec. 1, 2011

(86) PCT No.: PCT/FR2011/052844

§ 371 (c)(1),
(2), (4) Date: Aug. 13, 2013

(87) PCT Pub. No.: WO2012/072961

PCT Pub. Date: Jun. 7, 2012

(65) Prior Publication Data

US 2013/0324890 A1 Dec. 5, 2013

(30) Foreign Application Priority Data

Dec. 1, 2010 (FR) ..................................... 10 59965
Dec. 1, 2010 (FR) ..................................... 10 59967

(51) Int. Cl.
*A61B 5/00* (2006.01)
*A61B 5/11* (2006.01)
(Continued)

(52) U.S. Cl.
CPC . *A61B 5/11* (2013.01); *A61B 5/112* (2013.01); *A61B 5/6829* (2013.01); *G01C 21/165* (2013.01); *G01C 21/206* (2013.01); *G01C 22/006* (2013.01)

(58) Field of Classification Search
CPC ...... A61B 5/11; A61B 5/1116; A61B 5/1121; A61B 5/1122; A61B 5/1124; A61B 5/6801; A61B 5/6828; A61B 5/6829; A61B 5/6813; A61B 5/112; G01C 21/165; G01C 21/206; G01C 22/006
See application file for complete search history.

(56) References Cited

U.S. PATENT DOCUMENTS 7,467,060 B2 * 12/2008 Kulach ................. A61B 5/1112
702/141
8,988,438 B2 * 3/2015 Bang ................... G06K 9/00342
345/420

(Continued)

FOREIGN PATENT DOCUMENTS

| EP | 1 970 005 | 9/2008 |
|---|---|---|
| EP | 1 990 138 | 11/2008 |
| WO | 2007 093641 | 8/2007 |

OTHER PUBLICATIONS

Dejnabadi, H. et al., "Estimation and Visualization of Sagittal Kinematics of Lower Limbs Orientation Using Body-Fixed Sensors,", IEEE Transactions on Biomedical Engineering, IEEE Service Center, vol. 53, No. 7, pp. 1385 to 1393, (Jul. 1, 2006).

(Continued)

*Primary Examiner* — Max Hindenburg
(74) *Attorney, Agent, or Firm* — Oblon, McClelland, Maier & Neustadt, L.L.P.

(57) ABSTRACT

A method determining values of parameters representing a movement of an entity represented by an articulated chain, by a sensor assembly including at least one sensor for a parameter representing an orientation of a first segment of the articulated chain, the method including: reception of an orientation value measured and supplied by the orientation sensor; estimation of a value of at least one first parameter representing a movement of the first segment by processing the orientation value; and, based on a predetermined movement model of the articulated chain, as a time change model, including at least one relationship of time dependency between the at least one first parameter and at least one other parameter representing a movement of another segment of the articulated chain: estimation of a value of the at least one other parameter by application of the time change model to the estimated value of the at least one first parameter.

11 Claims, 10 Drawing Sheets

(51) Int. Cl.
*G01C 21/16* (2006.01)
*G01C 21/20* (2006.01)
*G01C 22/00* (2006.01)

(56) References Cited

U.S. PATENT DOCUMENTS

| | | | |
|---|---|---|---|
| 9,060,714 B2 * | 6/2015 | Bajcsy | .................... A61B 5/11 |
| 2008/0262772 A1 | 10/2008 | Luinge et al. | |
| 2008/0278497 A1 | 11/2008 | Jammes et al. | |
| 2008/0285805 A1 | 11/2008 | Luinge et al. | |
| 2009/0067678 A1 | 3/2009 | Caritu et al. | |

OTHER PUBLICATIONS

International Search Report Issued Nov. 7, 2012 in PCT/FR11/52844 Filed Dec. 1, 2011.

* cited by examiner

FIG. 11A
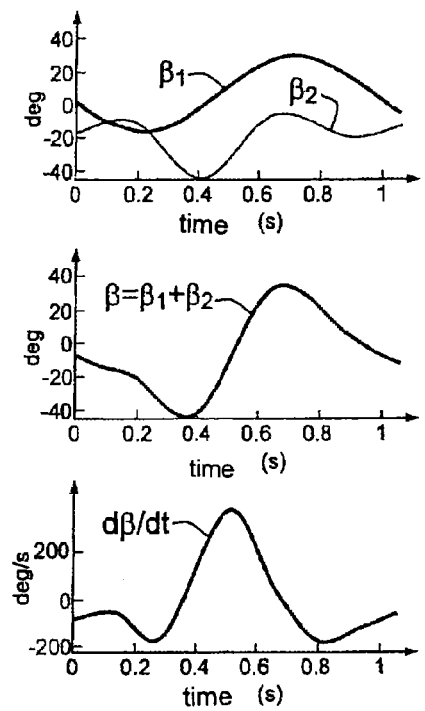
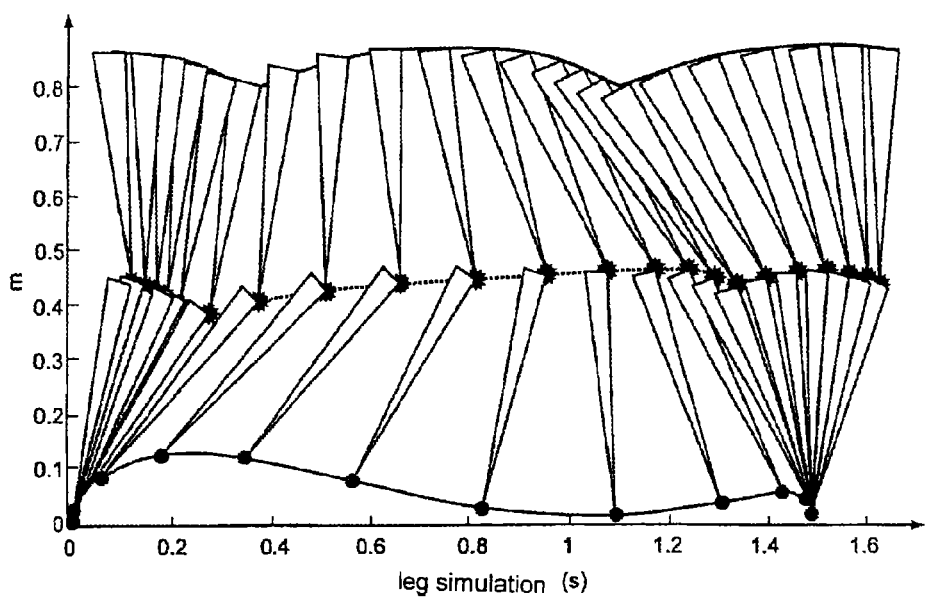
FIG. 11B

METHOD AND SYSTEM FOR DETERMINING THE VALUES OF PARAMETERS REPRESENTATIVE OF A MOVEMENT OF AT LEAST TWO LIMBS OF AN ENTITY REPRESENTED IN THE FORM OF AN ARTICULATED LINE

The invention relates to a system for determining values of parameters representing a movement of at least two limbs of an entity suitable for being represented in the form of an articulated chain. The purpose of this movement is to cause a movement of said entity.

An articulated chain is composed of articulations and substantially rectilinear rigid segments.

The parameters representing a movement of such an entity may be orientation (or angular position) and position (or cartesian position) parameters.

The movement of the entity may, for example, for an articulated chain representing the lower limbs of a living or artificial being (for example robotised), be a stepping movement, a running movement, a jumping movement, or a movement on a bicycle. For an articulated chain representing the upper limbs, the movement of the entity may for example be a movement by actuation or simulation of action of oars or paddles on a canoe, kayak or rowing boat.

In the case of a movement of an articulated chain, the movement of the articulated chain is characterised by the orientation and/or the position of a point of the segments of the articulated chain over time, or at least at particular instants.

For example, estimation of the position of the whole of an articulated chain may serve for navigation. One example of a navigation device is the GPS system, standing for "Global Positioning System", which is widely used at the present time. However, GPS poses problems in buildings or in a dense urban environment because of poor communication with the satellites. However, location has a certain interest inside buildings, for example for monitoring aged persons at their home, firefighters during their interventions, or visitors to an exhibition. Location by inertial sensor (using an accelerometer and/or a gyrometer and/or a magnetometer) may then be an advantageous alternative or complement to the GPS, since this is an autonomous system that is always available and is also less expensive than GPS.

Estimation of orientations may also be used, for example for analysing walking or running, or for medical, games or sports-training applications. Estimation of these orientations is all the more advantageous when the orientations are estimated for all the segments of the articulated chain. It is thus possible to represent movement studied overall (for example in order to animate an avatar or to study the angle of the knee or hip).

Movement capture systems are known that prove to be generally expensive or incapable of estimating both the position and the orientation of all the segments in the articulated chain used for locomotion.

The movement capture systems generally used, for example for cinema, comprise optical devices (systems marketed by Vicon or Codamotion), or magnetic devices (systems marketed by Polhemus). These devices are capable of estimating the movement (position and orientation) of the entire body but they are of high cost. In addition they require equipping the environment in which the movement takes place, and have a small coverage area.

Recently, movement capture systems based on electromechanical microsystems or MEMS, standing for "Micro-Electro-Mechanical System", have been developed. These devices, referred to as attitude units (marketed for example by Movea, Xsens and Microstrain) are generally composed of a triaxial magnetometer, a triaxial accelerometer and a triaxial gyrometer or a subassembly of these three movement sensors. They make it possible to estimate the orientation of the movable rigid body to which they are fixed, but not the position. In the case of an articulated chain, it is necessary to use one sensor per segment of the articulated chain for which it is sought to estimate the orientation. The installation of the system then proves to be difficult for the user. On the other hand, the coverage area is not reduced.

Systems have been proposed for merging the data of several inertial sensors disposed on the body with a biomechanical and/or articulated chain model.

The American patent application US 2008/0285805 proposes a method for capturing the movement of an object having at least two segments each equipped with at least one movement sensor. The measurements from the movement sensors are collected, each movement sensor comprising at least one triaxial accelerometer and one triaxial gyrometer (3A3G). The orientation and position of each segment is calculated by integrating the measurements delivered by the gyrometers and integrating twice the measurements delivered by the accelerometers, taking account in the calculations of stresses on the segments.

Their solution is general and does not take account of the specificity of the type of activity that uses complementary movements of several limbs. For example, in the case of walking, the movements of two limbs are similar and offset in time and the degrees of freedom of the two limbs are comparable. In addition, only embodiments systematically using at least one 3A3G sensor per limb are described, which is an embodiment having a large number of sensors, of high cost.

Patent application EP1984696 proposes a system for estimating the movement of an articulated chain consisting of N consecutive segments comprising means for measuring the acceleration of a segment of the chain and means for measuring the orientation on each of the segments. The presence of one sensor per segment being necessary, the system is of high cost.

Patent application EP 1 990 138 A1 relates to a method for estimating the movement of an articulated chain consisting of several segments. Each segment is equipped with a sensor and uses measurement models and an observer. Thus a large number of sensors is necessary and the cost and size are high. In addition, the algorithmic complexity is relatively high.

In order to study walking or navigation, devices are known using inertial sensors disposed on the lower limbs, in which the sensors are generally disposed on the foot or on the tibia and sometimes on the thigh.

For navigation, the systems can be grouped into two categories. A first category of systems uses relationships between parameters extracted from the measurements such as variance in acceleration or the length of steps, such as for example described in the American patent application U.S. Pat. No. 7,467,060. These relationships are of limited precision and vary from one user to another.

A second category of systems uses a double integration of the natural acceleration. These systems require using accelerometers. In order to obtain the natural acceleration, it is necessary to compensate for the gravity of the accelerometric measurements and therefore to know the orientation at each instant. These systems therefore also require either a sensor for estimating an angle such as a gyrometer and a magnetometer (WO 2010/046364), or an angular evolution model (US 2002/0002863).

These systems do not use information on the articulated chain and the performance/cost ratio is low.

These various systems have limited precision and high cost.

According to one aspect of the invention, a system is proposed for determining values of parameters representing a movement of at least two limbs of an entity for causing a movement of said entity, said entity being suitable for being represented in the form of an articulated chain, in which said at least two limbs connected together by an articulation each include at least one segment, the system being characterised in that it comprises:

means for measuring the value of a first parameter representing an orientation of a first segment of a limb of said chain;

for each other limb of said articulated chain, first means for determining the value of a second parameter representing an orientation of one of its segments;

second means for determining the value of a third parameter representing the change over time of a cartesian position of a point linked in movement to said articulated chain.

Such a system makes it possible, at low cost, to have the attitude of each of the segments of the articulated chain and the movement of any particular point on this chain.

In one embodiment, said measurement means comprise a magnetometer with at least one measurement axis and/or a gyrometer with at least one measurement axis.

Thus the size and cost are limited.

According to one embodiment, said first determination means comprise a magnetometer with at least one measurement axis and/or a gyrometer with at least one measurement axis fixed to each said other limb.

Thus the orientation of each of the segments may be obtained with improved precision. Moreover, the system adapts more rapidly to changes in speed.

In one embodiment, said first determination means are suitable for calculating the value of said second parameter(s) from the value of said first parameter by means of a time change model linking the values of said first parameter to those of the said second parameter(s).

Thus the number of sensors is minimised (it is not necessary to instrument all the limbs of the articulated chain).

According to one embodiment, said change model comprises an offset in time between the value of said first parameter and the value of said second parameter(s).

Thus the change model is simplified and takes into account a characteristic commonly encountered in the type of movement process.

In one embodiment, said change model is adapted to link the orientation of all the segments of said articulated chain to that of said first segment.

Thus the instrumentation of a single segment of the articulated chain makes it possible to go back to the orientation of all the segments of the articulated chain.

According to one embodiment, said second determination means comprise an accelerometer with at least two measurement axes.

Thus the precision can be improved.

In one embodiment, said articulated chain represents two upper limbs of a living or artificial being.

According to one embodiment, said articulated chain represents two lower limbs of a living or artificial being.

In one embodiment, said articulated chain comprises two segments per lower limb and six degrees of freedom.

Thus the placing of the lower limbs throughout a movement of the living or artificial being can be estimated with a minimised number of degrees of freedom and number of sensors.

According to one embodiment, said articulated chain comprises three segments per lower limb, and eight degrees of freedom.

Thus the sensor can be put on the foot (the least difficult case for the user and economically the most advantageous since the sensor can be in the shoe). If the time-change models linking all the angles are known, it is possible to refer back to all the angles in the articulated chain.

In one embodiment, said measurement means, said first determination means and said second determination means are suitable for being fixed to the articulated chain at a point corresponding to a tibia.

Thus the phases of placing the foot on the ground can easily be determined (angular sensors at the tibia).

In one embodiment, said measurement means, said first determination means and said second determination means are suitable for being fixed to the articulated chain at a point corresponding to the foot or ankle.

It is thus possible to use the zero speed information for limiting the drift due to the integration used for estimating the position.

According to one embodiment, the system comprises first means of detecting the placing on the ground of a foot of the articulated chain.

Thus the phases of the foot at zero speed are easily determined.

In addition, the system can comprise means of estimating the inter-foot distance.

Thus the system requires the instrumentation of only one limb, and the precision of the path of the feet can be improved.

In one embodiment, the system comprises second means for detecting movement cycles or particular instants characteristic of these cycles.

Thus it is possible to adjust the parameters of the time change models and to derive therefrom the movement over the duration of the cycle.

According to another aspect of the invention, a method for determining values of parameters representing a movement of at least two limbs of an entity in order to generate a movement of said entity is also proposed, said entity being suitable for being represented in the form of an articulated chain, comprising at least two segments connected by an articulation, characterised in that it comprises the steps consisting of:

measuring the value of a first parameter representing an orientation of a first segment of a first limb;

determining the value of one or more second parameters representing an orientation of a second segment belonging respectively to one or more other limbs of said articulated chain; and determining the value of a third parameter representing the change over time of a cartesian position of a point linked in movement to said articulated chain.

To this end, the subject matter of the invention is a method for determining values of parameters representing a movement by means of a sensor assembly, the movement involving at least two limbs of an entity represented in the form of an articulated chain in which each limb is itself represented by at least one segment and said at least two limbs are connected together by an articulation, the sensor assembly being fixed to the entity and comprising at least one sensor, referred to as the orientation sensor, for a parameter representing an orientation of a first segment of the articulated chain, this method comprising the following steps:

reception of an orientation value measured and supplied by the orientation sensor, estimation of a value of at least one first parameter representing a movement of the first segment by processing of the orientation value supplied, also comprising the following step, executed on the basis of a predetermined movement model of the articulated chain, referred to as the time-change model, comprising at least one relationship of time dependency between said at least one first parameter and at least one other parameter representing a movement of another segment of the articulated chain:

estimation of a value of said at least one other parameter by application of the time-change model to the estimated value of said at least one first parameter.

Thus the number of sensors is minimised (it is not necessary to instrument all the limbs of the articulated chain).

Optionally, the time-change model comprising a relationship of time dependency, in particular a relationship of time offset, between the movements of at least two distinct limbs of the entity, said at least one other parameter comprises a parameter representing a movement of another segment of the articulated chain associated with at least part of a limb of the articulated chain other than the limb represented at least by the first segment.

Also optionally, the time-change model comprises a relationship of time dependency of the orientations of all the segments of the articulated chain relative to that of the first segment.

Also optionally, the entity is represented in the form of an articulated chain representing two upper or lower limbs of a living or artificial being:

wherein each limb is itself represented by two segments connected together by an articulation, the articulated chain having six degrees of freedom, or wherein each limb is itself represented by three segments connected together in pairs by two articulations, the articulated chain having eight degrees of freedom.

Another subject matter of the invention is a computer program downloadable from a communication network and/or recorded on a medium readable by computer and/or executable by a processor, characterised in that it comprises instructions for executing the steps of a determination method according to the invention, when said program is executed on a computer.

Another subject matter of the invention is a system for determining values of parameters representing a movement, this movement involving at least two limbs of an entity represented in the form of an articulated chain in which each limb is represented by at least one segment and said at least two limbs are connected together by an articulation, comprising:

at least one sensor, referred to as the orientation sensor, for a parameter representing an orientation of a first segment of the articulated chain, this orientation sensor being provided with means for fixing to a part of the limb represented by this first segment, and means for processing orientation values measured and supplied by the orientation sensor, designed for implementing a determination method according to the invention.

Optionally, the orientation sensor comprises at least one of the elements of the assembly consisting of a magnetometer with at least one measurement axis and a gyrometer with at least one measurement axis.

Also optionally, a determination system according to the invention may comprise several orientation sensors, to the extent of at least one orientation sensor per limb of the entity.

Also optionally, a determination system according to the invention may also comprise an acceleration sensor with at least two measurement axes provided with means for fixing to the part of the limb represented by the first segment, for estimating cartesian position values for a point linked to the first segment.

Also optionally, a determination system according to the invention may also comprise at least one of the elements of the assembly consisting of first means of detection of the placing on the ground of a foot of the entity represented by said articulated chain, means for estimating an inter-foot distance and second means for detecting movement cycles or particular instants characteristic of these cycles.

The invention will be better understood from a study of a few embodiments described by way of in no way limitative examples illustrated by the accompanying drawings, in which.

Figure 4A:
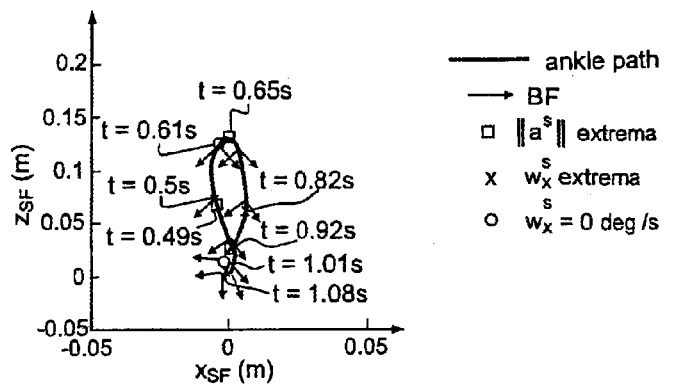
Figure 4B:
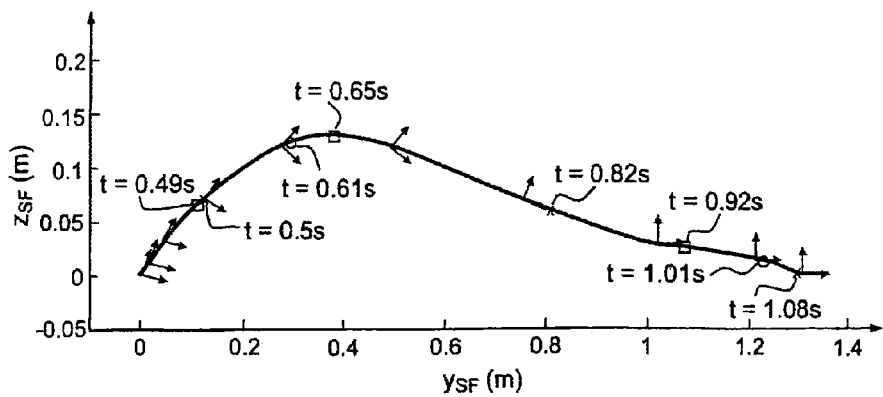
Figure 4C:
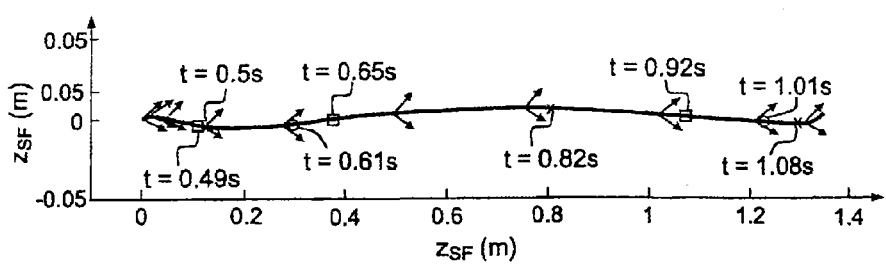
Figure 5:
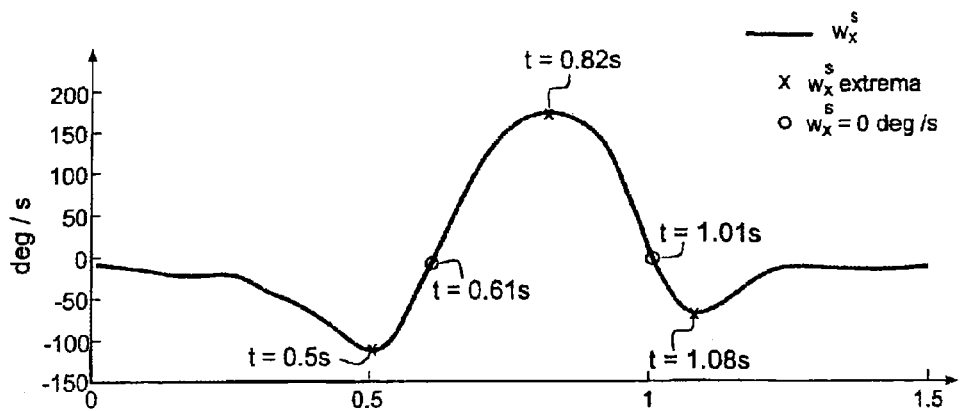
Figure 6A:
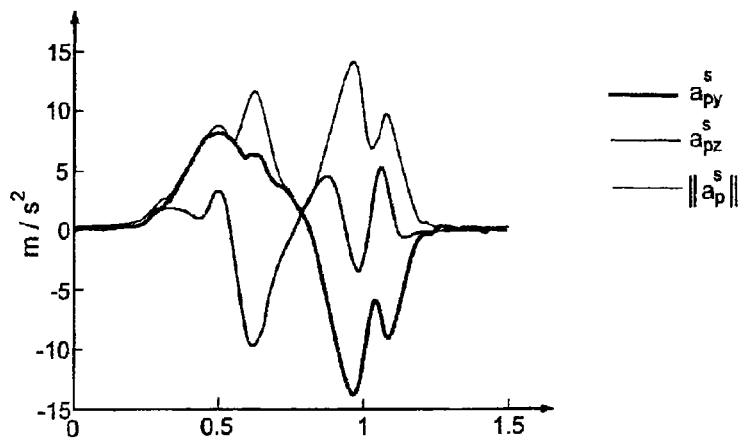
Figure 6B:
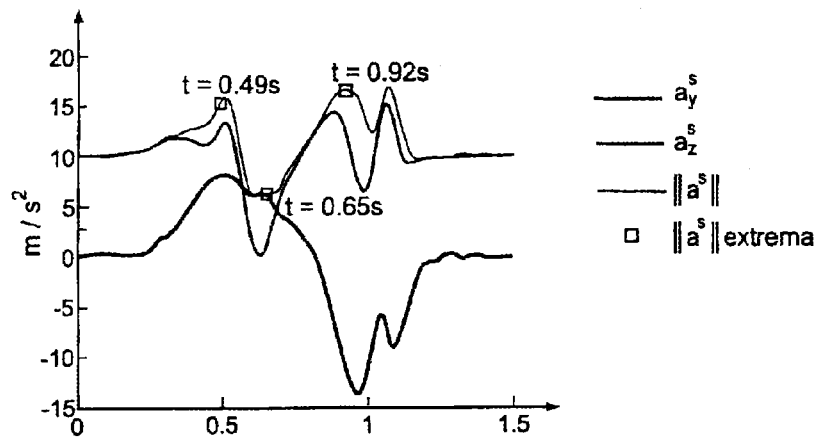
Figure 7A:
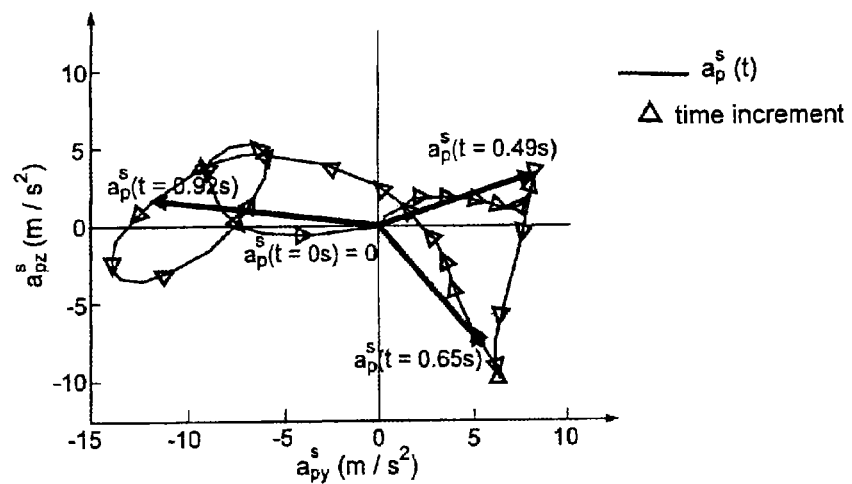
Figure 7B:
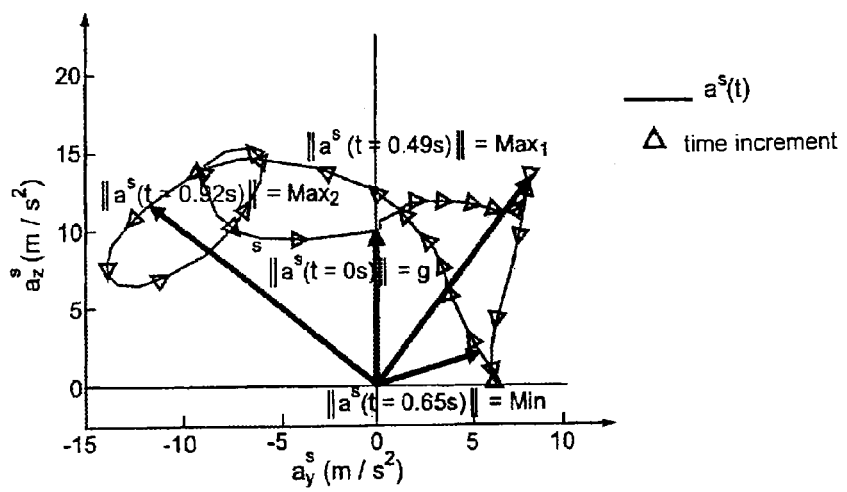
Figure 8A:
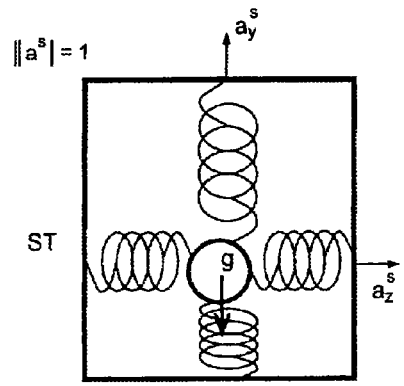
Figure 8B:
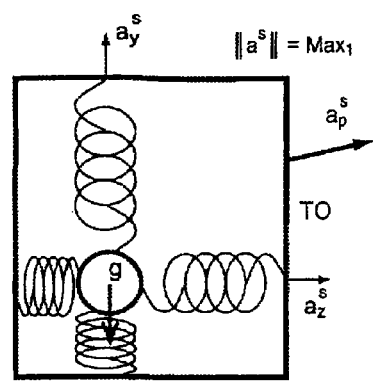
Figure 8C:
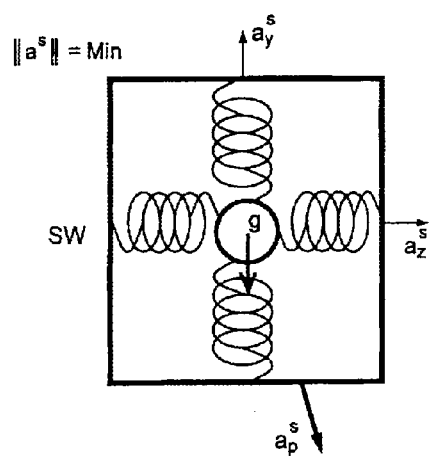
Figure 8D:
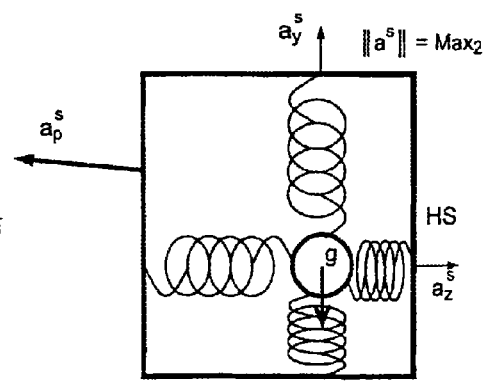
Figure 9A:
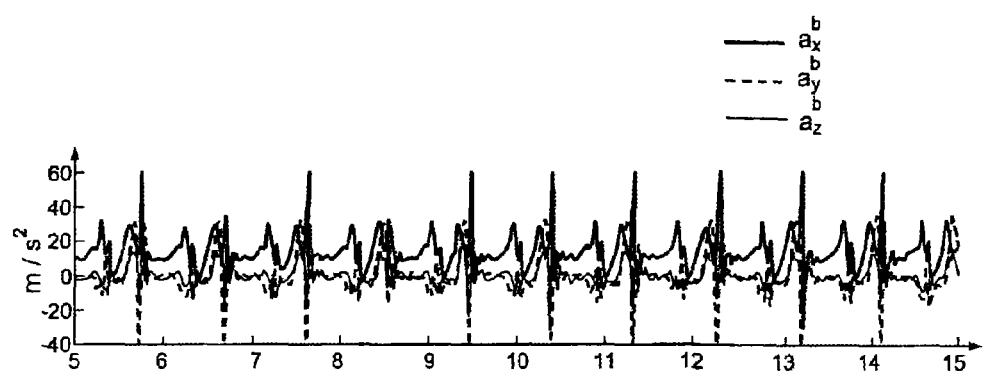
Figure 9B:
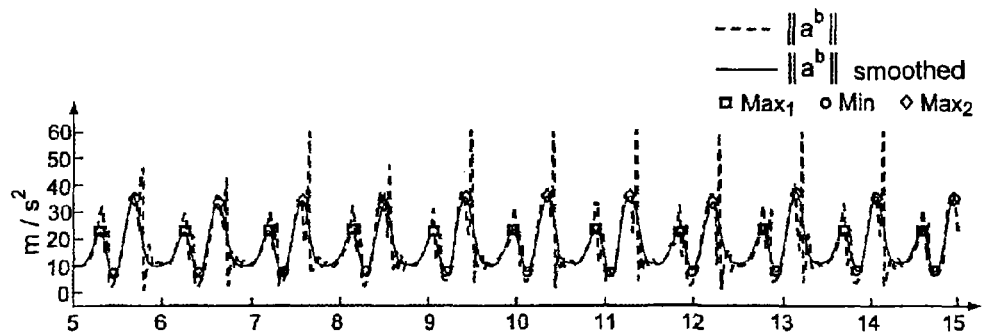
Figure 10A:
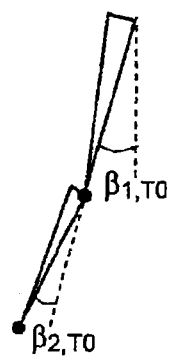
Figure 10B:
Figure 10C:
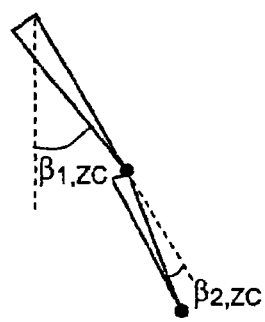
Figure 10D:
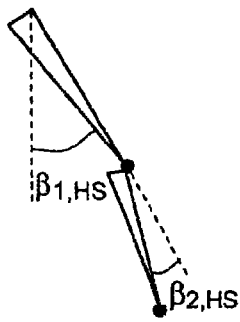
Figure 10E:

FIGS. 4A, 4B, and 4C illustrate the path of an ankle of a pedestrian during a walking cycle;

FIG. 5 illustrates the angular speed of the right foot of the pedestrian of the path in FIGS. 4A, 4B, and 4C;

FIGS. 6A and 6B illustrate respectively the instantaneous acceleration of the foot of the pedestrian calculated from the path of the foot and the measurement of an accelerometer expressed in the NF reference frame simulated from this acceleration;

FIGS. 7A and 7B illustrate the accelerations undergone by the ankle of the pedestrian during a walking cycle in FIGS. 4A, 4B, and 4C showing the norm and the direction of the acceleration, three acceleration vectors at three different instants are shown;

FIGS. 8A, 8B, 8C, and 8D show the operating principle of an accelerometer with two measurement axes having a seismic mass fixed to springs;

FIGS. 9A and 9B illustrate a step detection during the walking of a pedestrian from the norm of the acceleration measured by a sensor fixed to the ankle of the pedestrian, with a sampling frequency of 200 Hz;

FIGS. 10A, 10B, 10C, 10D, and 10E show the extrema values of the angles of a leg during a cycle of walking on foot;

FIGS. 11A and 11B show a simulation of the angles during walking;

FIGS. 12A, 12B, 12C, 12D, 12E, and 12F show the extrema of the angles of the legs during walking for different slopes; and FIGS. 13A and 13B, and 14A and 14B illustrate the functioning of a system according to an aspect of the invention comprising two triaxial magnetometers mounted on the ankles of a pedestrian.

In all the figures, the elements having the same references are similar.

Figure 1:
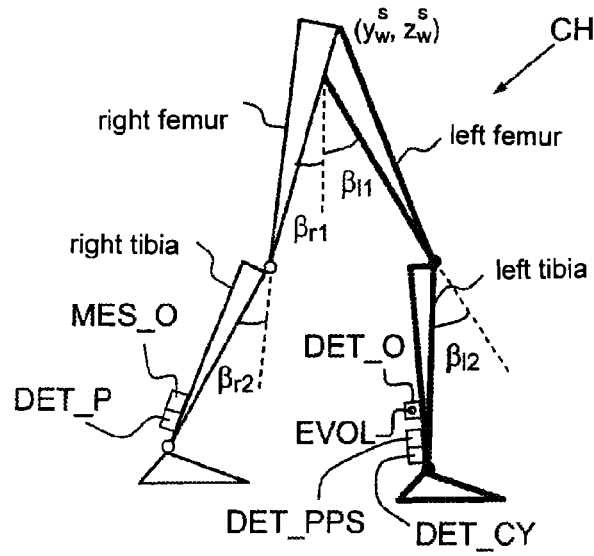
FIG. 1 illustrates an embodiment of a system according to one aspect of the invention.

FIG. 1 shows a system for determining values of parameters representing a movement of at least two limbs of an entity in order to generate a movement of said entity. The entity is suitable for being represented in the form of an articulated chain CH, comprising at least two segments connected by an articulation. In this case, the articulated chain of FIG. 1 comprises five articulations and six segments. The six segments are the two thighs, the two tibias and the two feet, and the five articulations are the hip, the two knees and the two ankles. Naturally this example of an articulated chain is not limitative. The knee, hip and ankle articulations are considered with one degree of freedom. The movement in a plane orthogonal to the rotation axes of the articulations is considered, these axes all being colinear. Thus the articulated chain comprises eight degrees of freedom, namely the angle of the various segments to the vertical and the cartesian position in two dimensions of a particular point on the articulated chain, for example the waist.

If in a variant it is considered that the articulated chain does not include the feet, and therefore not the ankles, but that the movement conditions are identical (in a plane orthogonal to the rotation axes of the various articulations, these various axes all being colinear), the articulated chain then comprises four segments, three articulations and six degrees of freedom.

During a given time range a point on the articulated chain CH is considered to be fixed. For example, during a part of the walking cycle, the foot is placed on the ground. Thus the position now depends only on the articular angles and the length of the segments, and the number of degrees of freedom is reduced.

In addition, the articular angles are bounded, i.e. lying between a minimum value and a maximum value, the articulations of the human body having articular stops.

The system comprises a module MES_O for measuring the value of a first parameter $\beta_r$ representing an orientation of a first segment of a first limb, in this case the right leg. The system further comprises a first module DET_O for determining the value of a second parameter $\beta_l$ representing an orientation of a second segment belonging to the other limb of the articulated chain CH, the left leg. When the articulated chain comprises more than two limbs, each other limb, different from the first limb provided with the measurement module MES_O, is provided with a respective module DET_O for determining the value of a second parameter representing an orientation of a second segment belonging to this other limb.

The system also comprises a second module DET_P for determining the value of a third parameter representing the change over time of a cartesian position P of a moving point linked to the articulated chain CH. The third parameter representing the change over time of a position P of a moving point linked to the articulated chain CH may be the cartesian position, the speed or the acceleration of the point P.

The measurement module MES_O may comprise a magnetometer with at least one measurement axis and/or a gyrometer with at least one measurement axis. The first determination module DET_O may comprise a magnetometer with at least one measurement axis and/or a gyrometer with at least one measurement axis fixed to a segment of the other limb.

The first determination module DET_O is adapted to determine, by means of a sensor and/or a change model, the value of said second parameters or parameters $\beta_l$ from the value of the first parameter $\beta_r$, by means of a time-change model EVOL linking the values of the first parameter $\beta_r$ to the values of said second parameter or parameters $\beta_l$.

The model EVOL may comprise an offset in time between the value of the first parameter $\beta_r$ and the value of said second parameter or parameters $\beta_l$.

In a variant, the model EVOL may be adapted to link the orientation of all the segments of said articulated chain to that of said first segment. The second determination module DET_P comprises, for example, an accelerometer with at least two measurement axes.

In a variant, the articulated chain CH may represent two upper limbs of a living or artificial being, in particular when the movement of the entity is for example a movement by actuation or simulation of actuation of oars or a paddle on a canoe, kayak or rowing boat. In this case, the thigh, tibia and foot segments are respectively replaced by the arm, forearm and hand segments.

The accelerometer may be adapted to be fixed to the articulated chain CH at a point corresponding to an ankle on a tibia.

The system may also comprise first means DET_PPS for detecting the placing on the ground of a foot in the articulated chain CH. It is then possible to take the position $P_r$ equal to $P_0$ throughout the duration of the step, $P_0$ being the last estimated position before the placing of the foot. The position $P_l$ of the other foot may be estimated by means of an estimation module EST_DIP able to retrieve the inter-foot distance, for example by means of a radio telemetric device. The inter-foot distance, associated with the change model, makes it possible to know where one is in the walking cycle for the second foot. Moreover, there is additional information on the length of the stride when the foot is placed, which improves the precision of the system. The use of a distance measurement system is only one example of use of the detection of the placing of a foot but it is very useful outside this particular embodiment.

The system may comprise second means DET_CY of detecting movement cycles. A cycle for walking corresponds to the succession of a step of each foot. This cycle corresponds to the pseudo-period between the occurrence of two similar events: between two instants at which the heel strikes the ground HS or between two lifts of the toes TO or between two instants where the foot is flat FF. In order to obtain the position and orientation of a point on the articulated chain, several means can be envisaged.

The positions are described by three cartesian coordinates in a reference frame linked to the terrestrial reference frame.

The orientations can be described by three angles or by a quaternion describing the rotations for passing from a reference frame linked to the terrestrial reference frame to a reference frame linked to the limb for which it is wished to measure the orientation.

Parameters representing the position and orientation means all or some of the variables expressing the position or orientation. The choice of these variables depends on the number of degrees of freedom of the articulated chain CH.

For example, in the case of walking forwards or backwards, only three items of information are needed: the two coordinates in the walking plane and the rotation angle about the medio-lateral axis.

One embodiment consists of positioning one inertial sensor per limb.

An inertial sensor, included in the measurement means MES_O, must be able to measure a parameter representing the orientation and position of the element to which it is linked. Thus an accelerometer with at least two measurement axes serves for measuring the position and a gyrometer with at least one measurement axis or a magnetometer with at least one measurement axis serves for measuring the orientation.

Preferentially, an inertial sensor is situated on the tibia at the ankle of each leg. Thus it is avoided having to estimate the angle of the foot. In addition, the proximity with the foot makes it possible to assume a zero speed when the foot is placed, and thus to avoid drift when integrating the natural acceleration issuing from the accelerometer.

The trajectory of each unit, used in the second determination module DET_P, is calculated by detecting the steps performed by the cycle detection module DET_CY and then the detection module DET_PPS, and then the calculation of the orientation at each measurement instant during the duration of the step. This orientation is used to express the measurement of the accelerometer in a reference frame linked to the terrestrial reference frame. This makes it possible to compensate for gravity and to use the assumption of zero speed at the start and end of the step. The natural acceleration thus obtained is then integrated twice. For example, in order to implement the second determination module DET_P, the system described in the patent application WO 2010/046364 will be taken.

Another solution makes it possible to minimise the number of sensors. For example, the path, determined by the second determination module DET_P, and the orientation, determined by the measurement module MES_O, of a point on a first limb is obtained by a first unit. The path of a point on the second limb and/or the orientation of the second limb is obtained by offsetting in time the signal from the first unit (raw signals from the sensors or treated, for position and orientation, obtained after treatment). This is because there often exists in locomotion a time relationship between the movements of the various limbs.

For example, in the case of walking, the movement of the limbs is offset by a half walking cycle. In the case of rowing the movement of the two arms is symmetrical.

Next, parameters of the articulated chain are calculated from the paths and angles.

Given the articulated chain model, it is possible to write the information previously calculated (angles by the modules MES_O and DET_O, and positions by the module DET_P) as functions of the parameters sought (articular angles, global position of the chain CH). The values of the parameters of the articulated chain CH are those that make it possible to verify the information previously calculated (angles and positions). These values can be obtained by any model reversal method (optimisation, Kalman filtering, geometry, etc.).

In one embodiment, the following notations are used:
The coordinates are given in the reference frame (Y, Z), Y being the axis given by the direction of walking and Z being the vertical axis upwards.
- $(y_w, z_w)$: Coordinates of the hip
- $(y_{al}, z_{al})$: Coordinates of the left ankle
- $(y_{ar}, z_{ar})$: Coordinates of the right ankle
- $\beta_{l1}$: angle of the left thigh with respect to the vertical
- $\beta_{l2}$: angle of the left tibia with respect to the left thigh
- $\beta_l$: angle of the left tibia with respect to the vertical
- $\beta_{r1}$: angle of the right thigh with respect to the vertical
- $\beta_{r2}$: angle of the right tibia with respect to the right thigh
- $\beta_r$: angle of the right tibia with respect to the vertical
- $L_{l1}$: length of the left thigh
- $L_{l2}$: length of the left tibia
- $L_{r1}$: length of the right thigh
- $L_{r2}$: length of the right tibia Describing the kinematics of the human body is very difficult. For example, a leg has 29 bones and 37 muscles. However, from analysis of the walking of pedestrians, the part of the legs of the pedestrians situated between the waist (the hips) and the ankle is modelled.

As illustrated in FIG. 1, during walking, the legs of the pedestrian are represented by four segments connected by three articulations. The femur and the tibia are represented by two rigid segments connected by an articulation representing the knee, with one rotation axis (one degree of freedom). The two legs of the pedestrian are connected at the femur with the waist, with a connection affording three degrees of freedom of rotation of the femur.

The concern is not with walking to the side or walking to the rear, but walking forwards. Consequently it is assumed that the femur has a single degree of freedom in the sagittal plane defined by the axes $(y_{SF}, z_{SF})$. Consequently the waist is represented by a single articulation to which the two legs are connected, affording two angles of rotation $\beta_{r1}$ and $\beta_{l1}$.

Thus the considered biomechanical model has six degrees of freedom and can be represented by four angles $\beta_{r1}, \beta_{r2}, \beta_{l1}, \beta_{l2}$ and the cartesian coordinates with two dimensions $(y_W^s, z_W^s)$ of the waist of the pedestrian.

$\beta_r$ and $\beta_l$ designate respectively the angles of the right and left tibias with respect to the descending vertical direction in accordance with the following equations:

$$\beta_r = \beta_{r1} + \beta_{r2}$$

$$\beta_l = \beta_{l1} + \beta_{l2} \quad (1a)$$

During walking the angles of the legs vary within a limited range and have a similar form for each step. The knee angles $\beta_{r2}$ and $\beta_{l2}$ must always be negative.

Hereinafter, $\beta$, $\beta_1$, and $\beta_2$ are used, for the two legs, to designate respectively $\{\beta_r, \beta_l\}$, $\{\beta_{r1}, \beta_{l1}\}$, and $\{\beta_{r2}, \beta_{l2}\}$.

In the remainder of this embodiment, it is possible to proceed in two ways:
- either, for each time sample, all the following steps are performed and iteration is carried out with the following sample;
- or each of the steps are performed over all the time samples during the duration of the step before passing to the following step.

The first solution is the one that results in the best performance.

Measurements are made with an accelerometer and a magnetometer on each tibia at the ankle.

In a variant, the measurements made on the second tibia may be obtained by making an offset in time of one half-cycle of a step of the measurements of the first tibia.

The path of each of the two feet and the angles $\beta_l$, $\beta_r$ of the tibias with respect to the vertical at each instant are calculated as for example described in the document WO 2010/046364. In this way six quantities are obtained (four positions and two orientations) $G = \{y_{al}, z_{al}, \beta_l, y_{ar}, z_{ar}, \beta_r\}$.

The above may, in a variant, be performed by an accelerometer and a gyrometer, or by an accelerometer, a magnetometer and a gyrometer fixed to the ankle, and a known method for estimating the path.

All the parameters representing the movement of the articulated chain CH can be described by a set PAR of parameters. In FIG. 1, the parameters to be determined are $PAR = \{y_w, z_w, \beta_{l1}, \beta_{l2}, \beta_{r1}, \beta_{r2}\}$. The known parameters are the set L of the lengths of the tibias and thighs: $L = \{L_{r1}, L_{r2}, L_{l1}, L_{l2}\}$.

A set PAR* of parameters is sought that best verify the information G. They can be obtained by seeking the parameters that minimise a distance, in the mathematical sense, between G and f(PAR*,L) with G=f(P,L); f representing the function that links the information G estimated previously to the known parameters of the articulated chain CH and to the parameters linked to the movement of this articulated chain CH.

This minimisation may, for example, be done by an optimisation algorithm such as the Levenberg-Marquard algorithm.

The function f is given by the following system of equations:

$$\begin{cases} y_{ra} = y_w + L_{r1}\sin(\beta_{r1}) + L_{r2}\sin(\beta_{r1} + \beta_{r2}) \\ z_{ra} = z_w - L_{r1}\cos(\beta_{r1}) - L_{r2}\cos(\beta_{r1} + \beta_{r2}) \\ \beta_r = \beta_{r1} + \beta_{r2} \\ y_{la} = y_w + L_{l1}\sin(\beta_{l1}) + L_{l2}\sin(\beta_{l1} + \beta_{l2}) \\ z_{la} = z_w - L_{l1}\cos(\beta_{l1}) - L_{l2}\cos(\beta_{l1} + \beta_{l2}) \\ \beta_l = \beta_{l1} + \beta_{l2} \end{cases} \quad (2a)$$

It is possible to add constraints. A constraint may be that the angle of the knee is always positive: $\beta_{l2} > 0$ and/or $\beta_{r2} > 0 > 0$. Another constraint may be that, when a foot is placed (left or right), its coordinates ($y_{la}$ and $z_{la}$ for the left foot placed and $y_{ra}$ and $z_{ra}$ for the right foot placed) are constant and equal to the coordinates estimated the first instant the foot is placed.

It is also possible to derive the above equations and to work on the speeds.

Figure 2:
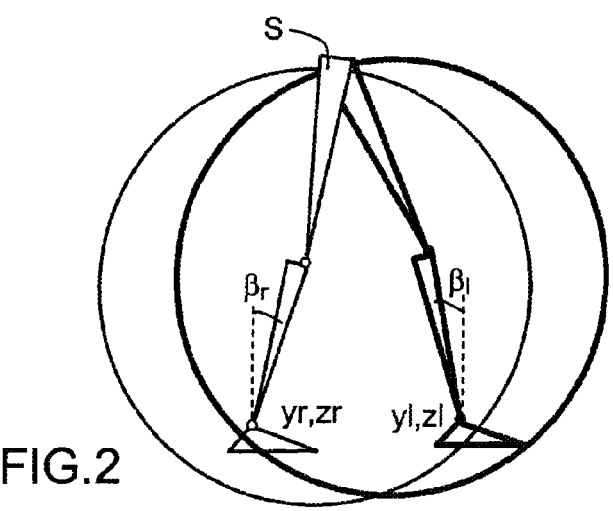
FIG. 2 illustrates an example of a geometric solution.

A geometric solution can be obtained as illustrated in FIG. 2.

For each leg, given the position of the ankle ($y_a, z_a$), the angle $\beta$ and the length of the tibia $L_2$, it is possible to determine the position of the knee. For this purpose a segment is traced representing the tibia having a first end of coordinates ($y_a, z_a$), a length $L_2$ and an orientation $\beta$ with respect to the vertical. The coordinates of the knee are then given by the coordinates of the other end of the segment. Thus it is then possible to trace a circle having at its centre the position of the knee and at its radius the length of the thigh. The hip is situated at the intersection of the two circles traced for the two legs. The hip cannot be situated below the ground. There is therefore a single solution S. Once the position S of the hip is determined, the segments of the thighs can be traced and the articular angles deduced.

Hereunder follows another embodiment of the invention, for an articulated chain CH representing two lower limbs of a living or artificial being.

A sensor of the measurement module MES_O is used to estimate a parameter representing the angle of at least one of the segments of the articulated chain CH.

An angle or angular velocity sensor is used, for example a magnetometer or a gyrometer with at least one measurement axis. The estimation of the angle or angular velocity using a magnetometer or gyrometer is known and is described hereinafter.

In an advantageous embodiment this sensor is positioned on a tibia. This is because, on a tibia, the change curve of the angles is richer, i.e. it has more singular points useful for the comparisons described in the remainder of the description.

In an advantageous embodiment, a sensor is positioned on each limb. This embodiment makes it possible to achieve the merger of two sensors in order to improve the precision of the system. It makes it possible, among other things, to take into account the changes in speed more precisely.

In an advantageous embodiment, a model EVOL for the change over time of the angle of at least one segment of the articulated chain CH is used. Thus, over time, the angles cannot change randomly but follow a change law that takes account of the movements made during the movement. This change model EVOL is characterised by minima and maxima.

An example of a change model may be a combination, linear or not, of trigonometric functions of time (such as cosine and sine) the frequency and amplitude of which are parameters to be determined. Advantageously, the angle between the thigh and the vertical is defined by a local minimum and a local maximum during each movement cycle of a substantially cyclic movement, for example a walking movement.

The angle between the thigh and the tibia is defined by two local minima and two local maxima defining the various phases of the walking cycle. The time-change curves EVOL of the various angles of the articulated chain CH are linked together. Thus the determination of an angle of a segment of the chain CH makes it possible to deduce the angles that are linked to it. This greatly reduces the number of sensors necessary.

The estimated angle can be compared with the angle of the change model EVOL, in order to determine at what point in the walking cycle it is situated, as well as the parameters of the angle-change model EVOL previously described.

One advantageous example of comparison consists of detecting local minima and/or maxima and/or zero crossings of the angle or angular velocity function. It is thus possible to determine the various phases of the walking as well as the value of the angles at particular instants during the walking: keeping the foot flat or FF, standing for "Foot Flat", corresponding to the maintenance of the pelvis above the foot; placing the foot on the ground or HS, standing for "Heel Strike", corresponding to the start of the damping phase that ends when the pelvis passes above the foot; the instant when the foot will leave the ground or TO, standing for "Toe Off"; the instant at which the foot goes forward again, or MS, standing for "Mid Swing", corresponding to the middle of the flight phase of the foot; the zero angular velocity instant or ZC, standing for "zero crossing", when the angular velocity passes through zero.

By means of the angle model EVOL and the values of the angles at these points, it is possible to adjust the parameters of the models and to derive therefrom the complete movement of the articulated chain CH between the points.

Among the parameters, it is possible to determine the inclination on the ground on which the user is moving, which is very useful for detecting climbs and descents.

For example, the reference frames are first defined and then the models of the measurements used are determined. The walking phases are then stated and a conventional way of detecting steps is given.

The vectors are measured in a reference frame linked to the sensor. Thus the measurements depend on the orientation of the sensor. As the sensors are attached to a moving body, the measurements are sensitive to instantaneous movements. This requires instantaneous measurements of rotation, since the attitude or orientation of the sensor changes over time.

Three reference frames are defined to clarify the transformations to be made in the remainder of the description. The North frame NF, the local frame BF, standing for "Body Frame", and the intermediate frame or SF, standing for "Step Frame", are respectively defined by the axes ($x_{NF}$, $y_{NF}$, $z_{NF}$), ($x_{BF}$, $y_{BF}$, $z_{BF}$), ($x_{SF}$, $y_{SF}$, $z_{SF}$) and the origins $O_{NF}$, $O_{BF}$, $O_{SF}$.

The North frame NF is a reference frame fixed with respect to the terrestrial reference frame during the whole of the movement, for example walking or running. The North frame NF can be considered to be the reference frame: the orientations or angular positions and the positions or cartesian positions are measured in this reference frame. The axes refer to the terrestrial reference frame through the directions East, North and Up. Its origin $O_{NF}$ can correspond to the place where the movement begins or to any other place. The data expressed in this reference frame are denoted with an exponent n.

The local reference frame, or the one linked to the sensor BF, is the reference frame in which the raw data are measured. Its centre is $O_{BF}$. The data in this reference frame are denoted with an exponent b. Its axes ($x_{BF}$, $y_{BF}$, $z_{BF}$) correspond to the axes of the sensors (in the case of triaxial sensors) at each instant. The coordinates of its origin $O_{BF}$ in the fixed global reference frame NF correspond to the location of the sensor in the fixed global reference frame NF at each instant.

The intermediate frame SF is a reference frame linked to the Earth, but only during an interval of time [$t_1$; $t_2$] (for example during a step). This frame is used with a movement sensor with fewer than six degrees of freedom or 6 DOF. For example, it is used when the movement sensor assembly EC has an invariant rotation axis and/or a flat movement during the interval of time [$t_1$; $t_2$]. $x_{SF}$ is the rotation axis and the sensor assembly EC is subjected to a flat movement in the plane defined by the axes ($y_{SF}$, $z_{SF}$). Whenever the plane is vertical, $y_{SF}$ is chosen for the horizontal axis while the axis $z_{SF}$ is the vertical axis. Its origin corresponds to the place of the sensor at the start of the interval of time (for example at $t=t_1$). The data expressed in this reference frame are denoted with an exponent s.

Figure 3:
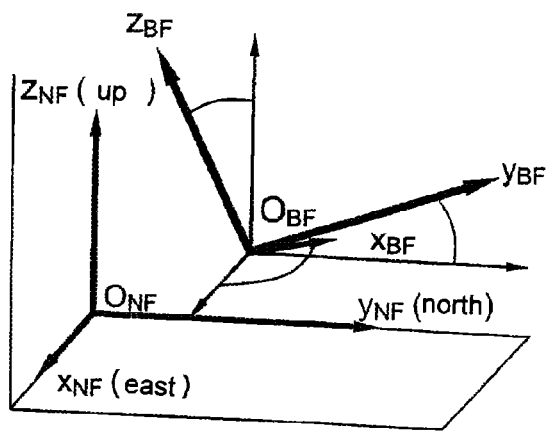
FIG. 3 shows the fixed NF and local BF global references.

FIG. 3 shows the fixed NF and local BF global frames. As can be seen, the local frame BF is linked to the fixed global frame NF by a translation and a rotation. All the inertial data are measured in the local frame BF. The local frame BF undergoes a translation and a rotation with respect to the fixed global frame NF.

The intermediate frame SF is linked to the fixed global frame NF by a translation that is invariant over time and a rotation invariant over time for the whole of the interval of time [$t_1$; $t_2$]. Here the local frame BF turns about the rotation axis $x_{SF}$ and, in some cases, it is assumed that the translation of $O_{BF}$, for t∈[$t_1$, $t_2$] is given in the plane defined by the axes ($y_{SF}$, $z_{SF}$). However, since the data measured are vectors, the interest relates particularly to the rotation between the frames in order to obtain the movement data in the fixed global frame NF.

The orientation of the fixed frame NF in the local frame BF with respect to the fixed frame NF can be expressed by the unit quaternion $q_{bn}$. The unit quaternion $q_{bn}$ is described with the rotation angle ψ about the rotation axis defined by the unit vector of direction $q_{bn}$ with three dimensions or with a unit vector with four dimensions as follows:

$$q_{bn} = \begin{bmatrix} \cos(\psi/2) \\ \sin(\psi/2)q_{bn} \end{bmatrix} = [q_{bn,0} \quad q_{bn,1} \quad q_{bn,2} \quad q_{bn,3}]^T \quad (1)$$

In the present application, all the quaternions are unit quaternions.

It can be noted that $q_{nb}$ is the conjugate of $q_{bn}$ and that:

$$q_{nb} = \begin{bmatrix} \cos(\psi/2) \\ -\sin(\psi/2)q_{bn} \end{bmatrix} = [q_{bn,0} \quad -q_{bn,1} \quad -q_{bn,2} \quad -q_{bn,3}]^T \quad (2)$$

To do this, a rotation matrix $R_{nb}$ is defined that makes the vector x, expressed in the frame BF linked to the sensor assembly, change to the same vector expressed in the fixed global frame NF by the following equation:

$$x^n = R_{nb} x^b \quad (3)$$

The inverse transformation matrix is $R_{bn} = R_{nb}^{-1} = R_{nb}^T$. In an equivalent manner, the matrix $R_{nb}$ is used to make a vector x, expressed in the fixed global frame NF, change to the same vector expressed in the frame BF linked to the sensor assembly.

The rotation matrix $R_{nb}$ is linked to the quaternion $q_{bn}$ by the following equation:

$$R_{bn} = \begin{bmatrix} 2q_{bn,0}^2 - 1 + 2q_{bn,1}^2 & 2q_{bn,1}q_{bn,2} - 2q_{bn,0}q_{bn,3} & 2q_{bn,1}q_{bn,3} + 2q_{bn,0}q_{bn,2} \\ 2q_{bn,1}q_{bn,2} + 2q_{bn,0}q_{bn,3} & 2q_{bn,0}^2 - 1 + 2q_{bn,2}^2 & 2q_{bn,2}q_{bn,3} - 2q_{bn,0}q_{bn,1} \\ 2q_{bn,1}q_{bn,3} - 2q_{bn,0}q_{bn,2} & 2q_{bn,2}q_{bn,3} + 2q_{bn,0}q_{bn,1} & 2q_{bn,0}^2 - 1 + 2q_{bn,3}^2 \end{bmatrix} \quad (4)$$

The model of the measurement supplied by the triaxial sensors used is now given.

Accelerometers measure the sum of all the accelerations applied to the sensor. On the Earth, accelerometers measure, in addition to terrestrial gravity, the external acceleration undergone by the sensor. Natural acceleration is defined by the external acceleration undergone by the sensor, which is equal to the derivative of the speed of the sensor.

Accelerometers have been used in numerous commercial, military and scientific applications, including inertial navigation, vehicle safety systems such as airbags, driving comfort control, stabilisation platforms and vibration monitoring. Commercial versions of triaxial accelerometers with orthogonal axes are widely used for all these applications, for which they are mounted fixedly on a moving body.

An accelerometer of the electromechanical microsystem or MEMS type comprises, among other components, a proof mass that is suspended elastically by one or more suspension springs. The proof mass m moves when the accelerometer undergoes an acceleration, and its movement $x_m$ is proportional to the force $f_m$ applied to the mass $$f_m = ma_x = -kx_m \quad (5)$$

in which k is the constant of the spring. The movement of the proof mass m is then converted into an electrical signal having an amplitude parameter that is proportional to the acceleration.

The acceleration measured includes terrestrial gravity as a shift of the acceleration of the body measured, and thus the acceleration of the body measured $a^b$ is linked to the natural acceleration $a_p^n$ by the following equation:

$$a^b(t) = R_{bn}(t)a^n(t) = R_{bn}(t)(a_p^n(t) - g^n) \quad (6)$$

in which t represents time, and $g^n = [0 \ 0 \ -g]^T$ represents the terrestrial gravity vector with g=9.81 m/s².

The Earth can be considered, as a first approximation, to be a magnetic dipole, with the south magnetic field pole S close to the magnetic north pole of the Earth, and the north magnetic field N close to the magnetic south pole of the Earth. The magnetic field varies from one place to another and differences in the terrestrial magnetic field may be due to the different nature of the rocks. Three magnetometers integrated on three orthogonal axes are used to measure the amplitude and orientation of the magnetic field, or in other words a triaxial magnetometer.

Although magnetic sensors are a little more difficult to use, they supply precise reliable data. In many commercial, military and scientific applications, magnetometers are included in particular for inertial navigation. Magnetometers also detect changes or perturbations in magnetic fields that have been created or modified. From these measurements, it is possible to derive, for example, information on the direction, presence, rotation, angle or presence of electric currents. In the absence of magnetic perturbations, it is assumed that the terrestrial magnetic field $b''$ in three dimensions, expressed in the frame NF invariant over time. For example, in France, $$b^n \approx \left[0 \frac{1}{2} \frac{-\sqrt{3}}{2}\right]^T h,$$

$h \approx 47$ μTesla. It is assumed hereinafter that the horizontal component of the terrestrial magnetic field $b''$ is along the axis $y_{NF}$.

The magnetic field $b^b$ measured in the local frame BF is given by the following equation:

$$b^b(t) = R_{bn}(t)(b^n + (t)) \quad (7)$$

wherein $T''$ designates the magnetic perturbation.

In the absence of any magnetic perturbation, $b''$ is deemed to be invariant over time: $b^b$ depends solely on the orientation of the sensor. However, the terrestrial magnetic field may be perturbed by metal constructions, electronic or electrical apparatus, etc. Consequently the measurements of the magnetometer are less reliable for determining the direction of the terrestrial magnetic field in certain situations, such as in an interior environment, and in particular close to walls or floors or ceilings, which generally comprise metal structures.

Certain properties of walking useful hereinafter are now described. First of all, the various phases of the walking cycle are defined as they are defined in the literature. The use of an optical movement capture system (of the Codamotion type) makes it possible to demonstrate a few particular properties of walking movement. More precisely, the movement of an ankle is represented by a substantially flat movement. This property is used in the present invention. Typical models are also analysed, observed on the measurements of the sensor during a walking cycle.

In this part, the spatio-temporal movement of an ankle is observed by means of a movement sensor comprising an accelerometer, a magnetometer or a gyrometer, mounted fixedly close to the ankle. The measurements supplied by the accelerometer and the variations in the attitude or orientation of the sensor during a step are observed.

During walking, the walking cycle is divided into two phases:
  a bearing phase, called ST, standing for "STance phase", during which the foot is in contact with the ground; and
  a flight phase, called SW standing for "SWing phase", during which the foot is not in contact with the ground.

In particular the walking cycle is characterised by several notable characteristic instants:
  maintenance of the foot flat or FF, standing for "Foot Flat", corresponding to the instant of the bearing phase at which the foot is on the ground, and the point and heel touch the ground;
  the instant when the foot will leave the ground or TO, standing for "Toe Off", which marks the transition between the stance phase ST and the swing phase SW;
  the instant at which the foot moves forward again or MS, standing for "Mid Swing", during the suspension phase, corresponding to the middle of the flight phase SW; and
  placing of the foot on the ground or HS standing for "Heel Strike", corresponding to the instant when the heel is in contact with the ground, representing the transition between the flight phase SW and the bearing phase ST.

In addition, the angular speed passes through the zero value on two occasions during a flight phase SW, respectively before and after the instant MS. A zero-crossing instant of the angular velocity and an instant of placing the foot on the ground HS are used hereinafter.

To study the behaviour of the ankle during a walk, using a three-dimensional optical movement capture system, called Coda CX1 by the company Charnwood Dynamics. Its main measuring unit contains three aligned cameras connected fixedly, which follow the position of a certain number of active markers (light-emitting diodes or infrared LEDs) in real time. The output of the system is recorded in a text file containing the coordinates in three dimensions of the active markers $P_{LED}^{(l)}$, where l designates the time index. The spatial precision is around 1 mm. With three markers on a rigid body, it is also possible to follow the orientation of the body. Thus three markers are fixed to the ankle of a pedestrian walking in front of the camera.

The position samples obtained are given in the reference frame of Coda CX1, which is linked to the reference frame NF and is defined by the position of the LEDs at the start of the walking. However, since we do not know this relationship and for reasons of clarity, the position samples are turned in order to correct or rectify the path of the ankle so as to have a horizontal stride and a movement in a vertical plane.

Consequently, v is determined, the unit vector orthogonal to the plane of the movement, with the smallest translation, by a singular value decomposition or SVD, applied to all the three-dimensional position samples $P_{LED} = [p_{LED}^{(l_1)} \ldots p_{LED}^{(l_2)}]^T$.

$l_1$ and $l_2$ are time indices, corresponding respectively to the start and end of a step. The vector v is the straight singular vector, i.e. the eigenvector associated with the smallest singular value or eigenvalue. The vector v is colinear with the axis $x_{SF}$, and it is assumed that the direction of the stride is colinear with the axis $y_{SF}$.

FIGS. 4A, 4B, and 4C show the path of the right ankle of a user during a step. The average speed of a pedestrian is approximately 0.6 m/s. As can be seen respectively in FIGS. 4A, 4B, and 4C, the variation along the axis $x_{SF}$ is less than 1 cm, while the variations along the axes $y_{SF}$ and $z_{SF}$ are respectively greater than 130 cm and 13 cm. The path represents a movement of an LED captured by a camera. The LED is fixed to the ankle of a pedestrian projected onto the planes ($x_{SF}$, $z_{SF}$), ($y_{SF}$, $z_{SF}$) and ($y_{SF}$, $x_{SF}$).

The instants when the foot will leave the ground TO and of placing the foot on the ground HS can be determined precisely from the two minima of the angular velocity measured.

FIG. 5 shows the extrema values of the angular velocity along the axis $x_{SF}$ deduced from the positions of the LED supplied by the Coda CX1 system: the zero crossing, and the instants TO and HS. As the variation in the path of the ankle along the axis $x_{SF}$ is negligible, the analysis is carried out in the plane of the step ($y_{SF}$, $z_{SF}$). FIG. 6A shows the natural acceleration $a_{py}^s$ and $a_{pz}^s$ during the interval of time of the step. The data are obtained from the path of the foot in FIGS. 4A, 4B, and 4C and smoothed with a low-pass filter with a cut-off frequency of approximately 20 Hz. FIG. 6B shows the acceleration for the same path as that of FIGS. 4A, 4B, and 4C, in the reference frame SF, by derivation of the measurements supplied by the Coda CX1 system. The difference between FIGS. 6A and 6B is that, in the second case, $a_z^s = a_{pz}^s + g$ and the data are smoothed with a low-pass filter with a cut-off frequency of approximately 10 Hz instead of 20 Hz. It is possible to see the impact of the cut-off frequency band (to be explained). FIG. 6B shows three critical instants that characterise the model $\|a^s\|$ (to be explained) when the curves pass through a first maximum at t=0.49 s, called $Max_1$, a minimum at instant t=0.65 s, called Min, and a second maximum at t=0.92 s, called $Max_2$. By detecting these extrema values, it is easy to detect the steps of the pedestrians, as explained in the remainder of the description. The instants corresponding to these extrema values are also visible in FIGS. 4A, 4B, and 4C, as well as the critical values of $\omega_x^s$.

To illustrate the variations in the measurements of the accelerometer, FIGS. 7A and 7B show the acceleration in the plane ($y_{SF}$, $z_{SF}$) and the associated instants. FIG. 7A shows the acceleration in two dimensions of FIG. 6A. FIG. 7B shows the acceleration of FIG. 6B in the reference frame SF.

As indicated previously, an accelerometer with two measurement axes can be considered to be a proof mass fixed to springs. FIGS. 8A, 8B, 8C, and 8D illustrate the behaviour of an accelerometer mounted on an ankle of a pedestrian in various situations. The accelerometer is shown at four moments, which refer to the phases ST and SW and the instants TO and HS. In the bearing phase ST, FIG. 8A, the natural acceleration is zero and the accelerometer measures only the acceleration due to gravity. The three extrema values of $a^s$ shown in FIG. 8B correspond to the instants TO, MS and HS. This can be explained by the orientation and the norm of the natural acceleration at these instants as in FIG. 7A, which are illustrated in FIGS. 8A, 8B, 8C, and 8D.

Many step detection methods are known. They are for example based on Fourier transformations, the counting of zero crossings of the output of an accelerometer or the counting of points that exceed a threshold ("In step with INS: navigation for the blind, tracking emergency crews" by Q. Ladetto and B. Merminod, GPS World, Vol. 13 (10), pp. 30-38, 2002).

Even if these methods are simple, they may suffer from significant errors when the users are walking on staircases, along a sloping ground, or when they run or drag their feet. Other precise methods are based on the angular variation of the foot and can estimate each phase of a step ("A magnetometer-based approach for studying human movements" by S. Bonnet and R. Heliot, IEEE Transactions on Biomedical Engineering, Vol. 54 (7), pp. 1353-1355, 2007).

In the present invention, a simple step detection is used. A practical solution for detecting the cycle of walking is to attach the sensor to the ankle of the pedestrian. Then, by means of acceleration or angular velocity measurements, the step is detected in a robust and reliable manner.

During its movement, the foot of a pedestrian follows almost the same form of path for the various steps. In fact, this is true even for different pedestrians who do not have any problem with walking. The acceleration norm $\|a^n\|$ measured is considered and its model is shown in FIG. 6B. The raw data measured contain, in addition to the noise, significant values at high frequencies in particular when the foot is placed on the ground HS. These high-frequency components are different from one step to another, and also for the same pedestrian, as well as for the same walking speed. Thus it is convenient to smooth the data before proceeding with the step detection. FIGS. 9A and 9B show the amplitude of the acceleration provided by a triaxial accelerometer fixed to the ankle of a pedestrian, for several walking steps. An example of smoothed acceleration data is illustrated in FIGS. 6A, 6B, 7A, and 7B.

Even if the trajectory of the ankle is similar for the various steps, the outputs of the sensor depend on the orientation of the sensor during the step. This problem is merely due to the orientation of the sensor on the heel at the start (of the step?). To overcome the problem of the variation in time of the orientation of the sensor on the ankle, it is possible to use simply the amplitude of the measurements of the accelerometer in the reference frame BF ("Robust step detection method for pedestrian navigation systems", by H.-J. Jang, J. W. Kim, and D. H. Hwang, Electronics Letters, 43 (14), 2007, in accordance with the following equation:

$$\|a^b(t)\| = \|R_{bn}(t)a^n(t)\| = \|a^n(t)\| \qquad (7)$$

Thus it is possible to use $\|a^b(t)\|$ since the model is equal to the model $\|a^n(t)\|$ (cf. the model in FIGS. 6A and 6B) and does not depend on the orientation of the sensor. On the other hand, for the angular velocity, it is possible to use $\omega_x^n$ (cf. the model in FIG. 5).

One solution is to compare this model with a model. Unfortunately, the model is often a version to a reduced scale in time and amplitude (to be clarified), which requires numerous signal processing operations. One practical solution consists of detecting the extrema values of the model, for example from a threshold crossing.

The aim is not only depth detection but also the determination of the start and end of the step. By means of this determination, it is possible to limit the drifts due to integration by fixing the zero speed at the start and end of the step.

Use is made of a system for monitoring the placing of a leg using only two sensors fixed respectively to the right ankle and to the left ankle of a pedestrian. The sensors may be 3A3M sensors (triaxial accelerometer and triaxial magnetometer), 3A3G sensors (triaxial accelerometer and triaxial gyrometer) or 3A3G3M sensors (triaxial accelerometer and triaxial magnetometer and triaxial gyrometer). The idea is to use the hypothesis of sagittal walking (in a vertical plane oriented in the anteroposterior direction on the median line of the body), in order to reduce the number of degrees of freedom for the model. Furthermore, a kinematic model of the legs is used, similar to those used in robotics. The sagittal plane hypothesis and the biomechanical model of the legs make it possible to solve the problem of estimation of the movement of the lower limbs and of navigation with a reduced number of sensors.

In the remainder of the description, the kinematic modelling of the legs of the pedestrian during walking is described. The parameters that define the model are designed to exploit the relationships between each part of the articulated chain CH of the system and for the walking phases. Next, an example of movement of the legs during walking is described using the simulation parameters. It is also described how to determine the parameters of the model, given the inertial data and the path of the pedestrian allowing spatio-temporal monitoring of the movement of the legs of the pedestrian.

The part of the legs of the pedestrian situated between the waist (the hips) and the ankle is modelled, as in the example described previously in the description of FIG. 1.

One way of modelling the variations in the angles of the legs is to interpolate them between the extreme values. FIGS. 10A, 10B, 10C, 10D, and 10E and 12e show the critical values of $\beta_1$ and $\beta_2$ during a step. $\beta_1$ increases from its minimum value to its maximum value between instants TO where the foot will leave the ground and the place of the foot on the ground HS. The value then decreases so as to once again reach its minimum value at the following instant TO where the foot will leave the ground. $\beta_2$ is characterised by four extreme values during a walking cycle. During the flight phase SW, $\beta_2$ varies from $\beta_{2,TO}$ to $\beta_{2,HS}$ and reaches its lowest minimum $\beta_{2,SW}$ (i.e. at the maximum flexing of the knee) and $\beta$ reaches its maximum $\beta_{ZC}$. During the bearing phase ST, $\beta_2$ varies from $\beta_{2,HS}$ to $\beta_{2,TO}$, during which it reaches another local extreme $\beta_{2,ST}$.

It is now shown how the model proposed above can imitate the walking of a human. The angles are simulated by fixing the parameters of the model so as to respect the critical angles previously shown in FIGS. 10A, 10B, 10C, 10D, and 10E. The angles $\{\beta_{1,TO}, \beta_{2,TO}\}$ and correspond respectively to the angles corresponding to the instants of TO where the foot will leave the ground and HS of placing the foot on the ground, while angles $\{\beta_{1,SW}, \beta_{2,SW}\}$ and $\{\beta_{1,ST}, \beta_{2,ST}\}$ correspond respectively to the local extrema of the angles during the flight SW and bearing ST phases, but not necessarily to those of the instants at which the foot moves forward again MS and maintaining the foot flat FF. The occurrence of these angles is examined in the remainder of the description.

A conventional solution for modelling the change over time of these angles is to use cosine functions. By way of example, FIGS. 11A and 11B show simulated angles $\beta_1$ and $\beta_2$. The angle $\beta_1$ is simulated with a cosine starting at the instant of placing the foot on the around HS.

$$HS \rightarrow ST \rightarrow TO \rightarrow SW \rightarrow HS \quad (9)$$

$$\beta_1(t) = \beta_{1,HS} + \frac{\beta_{1,TO} - \beta_{1,HS}}{2}\left(1 - \cos\left(2\pi \frac{t}{T_{gait}}\right)\right)$$

$T_{gait} = T_{Stance} + T_{Swing}$ is the duration of a walking cycle. The angle $\beta_2$ is simulated using four consecutive cosines, each representing the part of the model of the angles between two consecutive extrema:

$$HS \rightarrow ST: \beta_2(t) = \beta_{2,HS} + \frac{\beta_{2,ST} - \beta_{2,HS}}{2}\left(1 - \cos\left(\pi \frac{t}{T_{HS,ST}} + \beta_{12}\right)\right) \quad (10)$$

$$ST \rightarrow TO: \beta_2(t) =$$

$$\beta_{2,ST} + \frac{\beta_{2,TO} - \beta_{2,ST}}{2}\left(1 - \cos\left(\pi \frac{t - T_{HS,ST}}{T_{ST,TO}} + \beta_{12}\right)\right)$$

$$TO \rightarrow SW: \beta_2(t) =$$

$$\beta_{2,TO} + \frac{\beta_{2,SW} - \beta_{2,TO}}{2}\left(1 - \cos\left(\pi \frac{t - T_{HS,TO}}{T_{TO,SW}} + \beta_{12}\right)\right)$$

$$SW \rightarrow HS: \beta_2(t) =$$

$$\beta_{2,SW} + \frac{\beta_{2,HS} - \beta_{2,SW}}{2}\left(1 - \cos\left(\pi \frac{t - T_{HS,SW}}{T_{SW,HS}} + \beta_{12}\right)\right)$$

$T_{HS,ST}$, $T_{ST,TO}$, $T_{TO,SW}$ and $T_{SW,HS}$ designate the intervals of time separating the extrema corresponding to the indices. The angle $\beta_{12}$ is a phase angle between $\beta_1$ and $\beta_2$. The angle $\beta_{12}$ is explained below in the description, where its dependency with the slope of the walking is demonstrated.

FIGS. 11A and 11B illustrate a simulation of walking in which the angles of the left and right legs follow the equations (9) and (10) with a relative delay time $T_{gait}/2$ between the left and right angles. FIGS. 11A and 11B show respectively the angular time variations and the leg movements of the biomechanical model. In this case, $T_{HS,ST} = T_{ST,TO} = T_{TO,SW} = T_{SW,HS} = T_{gait}/4$ has been taken.

The extrema are given for this simulated walking in the following table, as well as $\beta_{12}$. $L_F$ and $L_T$ represent the length of the segments representing respectively the femur and tibia.

| $\beta_{1,TO}$ | $\beta_{1,HS}$ | $\beta_{2,TO}$ | $\beta_{2,SW}$ | $\beta_{2,HS}$ | $\beta_{2,ST}$ | $\beta_{12}$ | $L_F$ | $L_T$ |
|---|---|---|---|---|---|---|---|---|
| −15° | 30° | −10° | −45° | −5° | −25° | 20° | 43 cm | 45 cm |

Finally, assuming that the ankle does not move during a bearing phase ST (assuming the speed of the ankle to be zero), the coordinates $(y_W^s, z_W^s)$ can be calculated. This is because, knowing the position of a point on the chain (here the ankle on the ground) and all the articular angles (given by equations (9) and (10) and the position in the walking cycle), it is possible to determine the position of any point on the chain (in this case the hip).

FIGS. 11A and 11B show the path of the ankle calculated from the simulated angles. It is clear that this simulated path is typical of a pedestrian ankle. It can be remarked that these angles are modelled using the critical angles in FIGS. 10A, 10B, 10C, 10D, and 10E. It is assumed hereinafter that the critical angles of FIGS. 10A, 10B, 10C, 10D, and 10E represent typical walking.

There are two ways of determining the slope during walking from the angles $\beta_1$ and $\beta_2$.

Figure 12A:
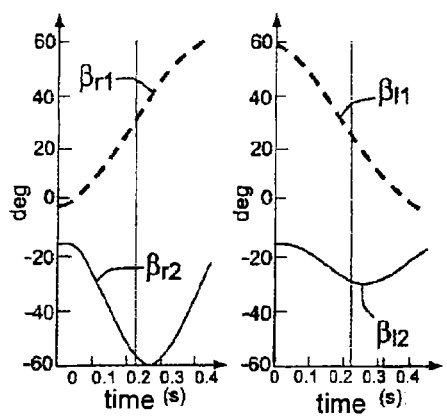

The first way of determining the slope (or the angle between the horizontal and the vector of the movement during a step) is based solely on the extrema of $\beta_1$ that increase with the slope or inclination. FIGS. 12A, 12C, and 12E represent three values of $\beta_1$ associated with three slopes shown respectively in FIGS. 12B, 12D, and 12F. To determine the slope during walking, the absolute angle $\beta_1$ with respect to the vertical is necessary.

The second way of determining the slope is to use the relationship between the phase angle $\beta_{12}$ in equations (10) and the slope of the step. In practice, the phase $\beta_{12}$ is almost equivalent to the interval of time between the instant at which the foot moves forward again MS and the minimum value of $\beta_2$.

Figure 12B:
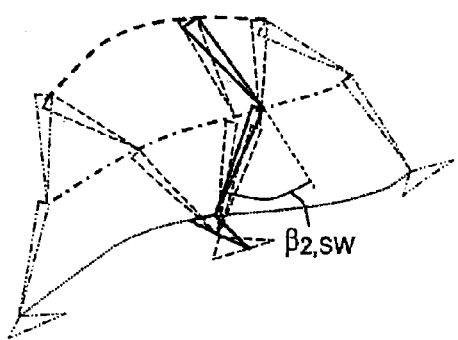
Figure 12C:
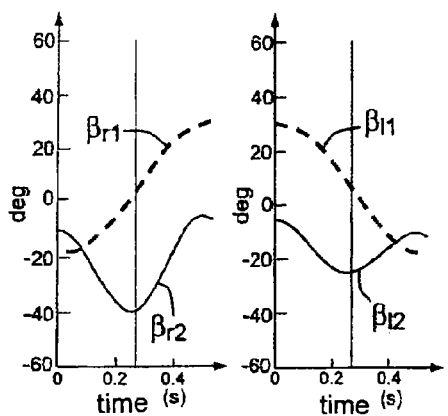
Figure 12D:
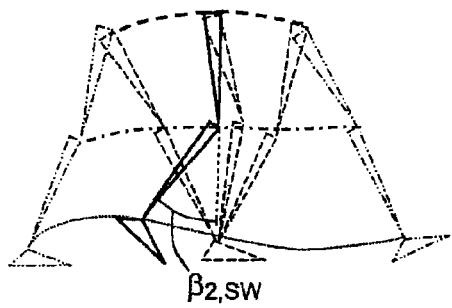
Figure 12E:
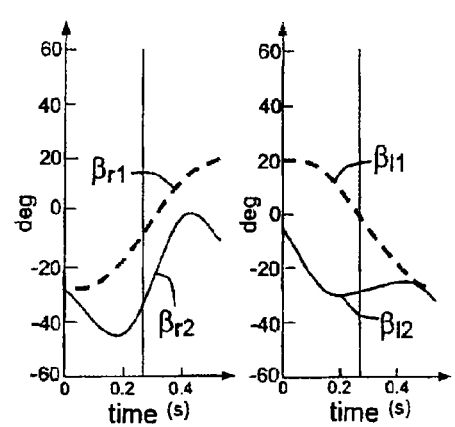
Figure 12F:
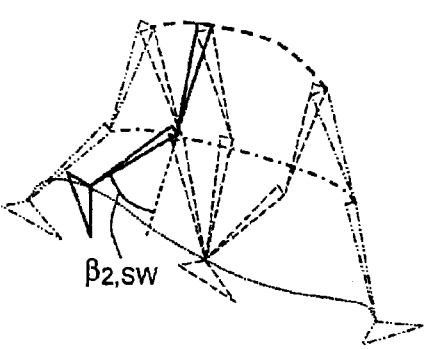

FIGS. 12A, 12B, 12C, 12D, 12E, and 12F show the angular change models for various slopes. When the slope changes, the moment when the minimum value of $\beta_2$ is reached during the flight phase SW ($\beta_{2,SW}$) changes with respect to the instant at which the foot moves forward again MS. Thus the occurrence of $\beta_{2,SW}$ depends on the angle of the slope. For example, FIGS. 12A, 12B, 12C, 12D, 12E, and 12F show that $\beta_{2,SW}$ produces:

at the end of the flight phase SW (for example after the instant MS at which the foot moves forward again, as in FIG. 12A, with a rise (cf FIG. 12B);

at the middle (for example close to the instant MS at which the foot moves forward again, as in FIG. 12C) with a zero slope (cf FIG. 12D);

at the start of the flight phase SW (for example before the instant MS at which the foot moves forward again, as in FIG. 12E) with a descent (cf FIG. 12F).

In fact, when a pedestrian walks on a given slope, his waist (his hips) follows a path with a constant slope. As the pedestrian must move his foot above the ground, the minimum value $\beta_{2,SW}$ is reached when the line connecting his waist and his foot in the air becomes orthogonal to the ground.

As indicated previously, the two-dimensional biomechanical model of FIG. 1 has six degrees of freedom. It is shown how to estimate/predict the six parameters (i.e. $\beta_{l1}$, $\beta_{l2}$, $\beta_{r1}$, $\beta_{r2}$, $y_W^s$, $z_W^s$) using the angles $\beta_r$ and $\beta_l$ of the right and left tibias defined in equation (1a). Finally, the experimental results using two magnetometers fixed to the ankles showing the orientation and position of the legs of the pedestrian during walking are presented.

Generally, during walking, at least one of the feet touches the ground. It can therefore be assumed that the speed of the ankle is equal to zero during the bearing phase ST. With this assumption and knowing the rotation movement of the legs, it is possible to determine the speed of the waist (hips). Consequently, if all the four angles $\{\beta_{r1}, \beta_{r2}, \beta_{l1}, \beta_{l2}\}$ are known, it is then possible to calculate $(y_W^s, z_W^s)$ according to the angles of the leg that is in the bearing phase ST. Let $(x_{RK}^s, y_{RK}^s, z_{RK}^s)$, $(x_{LK}^s, y_{LK}^s, z_{LK}^2)$, $(x_{RA}^s, y_{RA}^s, z_{RA}^s)$ and $(x_{LA}^s, y_{LA}^s, z_{LA}^s)$, be the coordinates of the right and left knees and the right and left ankles respectively, where all the coordinates $x^s$ are equal to zero. The placing of the legs is constructed and the coordinates are calculated as follows:

$$\begin{aligned} y_W^{s(l)} &= y_W^{s(l-1)} + \delta_y^{(l)} & z_W^{s(l)} &= z_W^{s(l-1)} + \delta_z^{(l)} \\ y_{RK}^{s(l)} &= y_W^{s(l)} + L_F \sin\tilde{\beta}_{r1}^{(l)} & z_{RK}^{s(l)} &= z_W^{s(l)} - L_F \cos\tilde{\beta}_{r1}^{(l)} \\ y_{LK}^{s(l)} &= y_W^{s(l)} + L_F \sin\tilde{\beta}_{l1}^{(l)} & z_{LK}^{s(l)} &= z_W^{s(l)} - L_F \cos\tilde{\beta}_{l1}^{(l)} \\ y_{RA}^{s(l)} &= y_{RK}^{s(l)} + L_T \sin\beta_r^{(l)} & z_{RA}^{s(l)} &= z_{RK}^{s(l)} - L_T \cos\beta_r^{(l)} \\ y_{LA}^{s(l)} &= y_{LK}^{s(l)} + L_T \sin\beta_l^{(l)} & z_{LA}^{s(l)} &= z_{LK}^{s(l)} - L_T \cos\beta_l^{(l)} \end{aligned} \quad (11)$$

Whereas the "$\beta$" values were obtained with the measurement means MES_O, the values denoted "$\tilde{\beta}$" are deduced using the change models EVOL (equations (9) and (10)) and certain hypotheses that link $\beta_1$ and $\beta_2$ to $\beta$ (equation (19) for example).

$(\delta_y^{(l)}, \delta_z^{(l)})$ defines a translation of the waist (hips) so as to verify the bearing phase ST. Thus:

if the right ankle is in the bearing phase ST:

$$\delta_y^{(l)} = y_{RA}^{s(l-1)} - y_W^{s(l-1)} - L_F \sin(\tilde{\beta}_{r1}^{(l)}) - L_T \sin(\beta_r^{(l)})$$

$$\delta_z^{(l)} = z_{RA}^{s(l-1)} - z_W^{s(l-1)} + L_F \cos(\tilde{\beta}_{r1}^{(l)}) + L_T \sin(\beta_r^{(l)}) \quad (12)$$

if the left ankle is in the bearing phase ST:

$$\delta_y^{(l)} = y_{LA}^{s(l-1)} - y_W^{s(l-1)} - L_F \sin(\tilde{\beta}_{l1}^{(l)}) - L_T \sin(\beta_l^{(l)})$$

$$\delta_z^{(l)} = y_{LA}^{s(l-1)} - z_W^{s(l-1)} + L_F \cos(\tilde{\beta}_{l1}^{(l)}) + L_T \sin(\beta_l^{(l)}) \quad (13)$$

As the two-dimensional cartesian coordinates of the waist of the pedestrian can be calculated once the four angles of the legs have been determined, the problem is reduced to four degrees of freedom.

The placing of the legs with four degrees of freedom can be determined by all the four angles $\{\beta_{r1}, \beta_{r2}, \beta_{l1}, \beta_{l2}\}$. The most simple means of determining these angles is to attach a movement sensor to each segment of the biomechanical model (two femurs and two tibias). However, since we assume that, during walking, the segments turn on an orthogonal invariant axis and move in a plane orthogonal to this axis, it is not necessary to determine the orientation in three dimensions in order to construct the biomechanical model. Thus the minimum solution consists of positioning a magnetometer with two measurement axes 2M in a plane orthogonal to the rotation axis or a gyrometer with one measurement axis 1G parallel to the rotation axis (medio-lateral in the case of normal walking). Another solution consists of dispensing with the orientation of the sensor with respect to the segment by using a triaxial magnetometer 3M or a triaxial gyrometer 3G attached to each part of the legs of the pedestrian (i.e. the four segments). It is also assumed that the movement sensor turns about an axis invariant over time, and it is possible to determine the axis of the rotation. Thus the angle of each segment of the biomechanical model can be determined.

Furthermore, reducing the number of sensors is more practical for daily use. In addition, this reduces the cost and the electrical consumption of the whole of the navigation system. Consequently two movement sensors are used fixed to the left and right ankles, enabling the placing of the legs of the pedestrian to be monitored. This method has been applied in an external environment where the magnetometers fixed to an ankle are not interfered with. Thus it is possible to determine the position from the magnetometer mounted on the ankle. In a monitoring of placing of the legs of the pedestrian indoors, a magnetometer close to the floor is greatly disturbed. Thus another movement sensor may be used for determining the position. For example, a third movement sensor mounted on the waist of the pedestrian can be used to monitor the position of the pedestrian.

Hereinafter the estimation of the placing of the legs of the pedestrian using the two movement sensors mounted on the ankles is focused on.

Determining the placing of the legs for the biomechanical model requires knowledge of the four angles. Consequently it is necessary to deduce four degrees of freedom from $\beta_l$ and $\beta_r$. One solution consists of reducing the four degrees of freedom of the model to two degrees of freedom, the number of angles available. For example, the possibility of establishing functions of time for the angles $\{\beta_{r1}, \beta_{r2}, \beta_{l1}, \beta_{l2}\}$ using the cosine functions is shown previously. By means of these functions, only one angle is necessary for determining the whole of the placing of the legs, reducing the model to one degree of freedom instead of four. However, this method lacks precision. Furthermore, the slope of the walking changes the time occurrence and the value of the extrema of angles $\{\beta_{1,TO}, \beta_{1,HS}, \beta_{2,TO}, \beta_{2,SW}, \beta_{2,HS}, \beta_{2,ST}\}$ as described previously, which makes a universal equation very complex to establish.

Another solution consists of using the implicit information included in the angles $\beta_l$ and $\beta_r$, in addition to the angles themselves. This information makes it possible to predict four angles from the two unknown angles by relying on equations of angles relating to the walking of a pedestrian. It is proposed to interpolate the angles $\beta_{r1}$ and $\beta_{l1}$ while relying on the critical values and their instants of occurrence, and the zero crossings of the angular velocities $d\beta_r/dt$ and $d\beta_l/dt$, where $\text{Max}_1$ and $\text{Max}_2$ are respectively achieved at instant TO where the foot will leave the ground and that instant HS of placing the foot on the ground, while the zero crossings correspond to the maximum value of $\beta$.

The angles $\beta_r$ and $\beta_l$ are now determined. It is possible to use a magnetometer with at least two measurement axes 2M or a gyrometer with at least two measurement axes 2G or a gyrometer with one measurement axis G for determining the angles $\beta_r$ and $\beta_l$. When a triaxial magnetometer 3M or a triaxial gyrometer 3G is used, it is then possible to dispense with the orientation of the sensor with respect to the segment and to determine $\beta_l$ and $\beta_r$ by estimating first the rotation axis of the segment in the reference frame of the sensor. Let all the three singular vectors issuing from the SVD of the matrix of measurements (rows=all the measurements during the step and column=the 3 axes) be noted $(v_1^b, v_2^b, v_3^b)$, where $(v_1^b, v_2^b)$ are associated with the plane of the walking and $v_3^b$ the axis of the rotation substantially invariant over time expressed in the reference frame of the sensor BF. With the measurements $\omega^b$ of the gyrometer, it is possible to obtain the angular velocity about the axis $v_3$, in accordance with the following equation:

$$\omega_{v_3}(t) = \omega^b(t) \cdot v_3^b \quad (14)$$

in which "·" designates the scalar product. Next the angular velocity $\omega_{v_3}(t)$ is integrated in order to give the following equation:

$$\beta(t)=\beta(t_0)+\int_0 \omega_{v_3}(t)dt \qquad (15)$$

$t_0$ is the instant FF of maintaining the foot flat during the bearing phase ST, determined by a detection method for identifying the various phases of walking (EP 2106747), $\beta(t_0)$ is the angle of the tibia with respect to the vertical at instant $t=t_0$.

Likewise, $\beta(t)$ can be calculated using $b^b(t)$ by the following equation:

$$\beta(t)=\beta(t_0)+\beta_b \qquad (16)$$

in which:

$$\beta_b(t) = \text{sine}(\lfloor v_3^b \quad b^b(t) \quad b^b(t_0) \rfloor)\text{atan}\left(\frac{\|(b^b(t) \wedge v_3^b) \wedge (b^b(t_0) \wedge v_3^b)\|}{(b^b(t) \wedge v_3^b) \cdot (b^b(t) \wedge v_3^b)}\right) \qquad (17)$$

$\wedge$ representing the vectorial product.

To determine $\beta(t_0)$, an observation of $\beta$ at $t=t_0$ is needed:
  the first solution consists of having prior knowledge of the angle $\beta(t)$, for example a critical value at the instants of FF, HS, TO, MS and ZC;
  the second solution consists of using inertial measurements. The orientation of the movement sensor relative to the tibia must be known (i.e. an axis of the reference BF must be aligned with the tibia).

It is assumed that $z_{BF}$ is aligned with the direction of the tibia. If an accelerometer is used, its measurements at the instant FF of maintaining the foot flat (on a flat ground) is $a^b(t_0)=g^b$, $\beta(t_0)$ being able to be determined as the angle between $z_{BF}$ and the vertical given by $a^b(t_0)=g^b$, $z_{BF}$ and $a^b(t_0)$ both being projected into the plane of the walking.

$$\beta(t_0) = \text{sine}(\lfloor v_3^b \quad a^b(t_0) \quad z_{BF}^b \rfloor)\text{atan}\left(\frac{\|(a^b(t_0) \wedge v_3^b) \wedge (z_{BF}^b \wedge v_3^b)\|}{(a^b(t_0) \wedge v_3^b) \cdot (z_{BF}^b \wedge v_3^b)}\right) \qquad (18)$$

After having calculated $\beta_r$ and $\beta_l$ using equations (16), (17) and (18), the placing of the legs can be estimated.

It can be remarked that the occurrences of the maximum of $\beta$ and $\beta_l$ are relatively close (cf FIGS. 11A and 11B). Hereinafter, it is assumed that:
  $\beta_1$ reaches its maximum when $\beta$ reaches its maximum (i.e. at the zero crossing of $d\beta/dt$);
  $\beta_{r1}$ reaches its minimum when $\beta_{l1}$ reaches its maximum and vice-versa.

Let $t_{ZC}^\kappa$ be the instant of zero crossing of $d\beta/dt$ for step number $\kappa$ when $\beta_r$ or $\beta_l$ reaches a local maximum. $\kappa$ is incremented at each zero crossing when $\beta_r$ or $\beta_l$ reach their maximum value. Hereinafter, these critical moments are concentrated on in order to interpolate $\beta_1$.
  each step $\kappa$, $\beta_{r1}^\kappa$ and $\beta_{l1}^\kappa$ are interpolated with two cosine functions, for $t\in I_{ZC}^\kappa$, with:
    $I_{ZC}^\kappa = [t_{l,ZC}^{\kappa-1}, t_{r,ZC}^\kappa]$ when $\beta_{r1}$ increases from its minimum value (calculated previously at the zero crossing at step $\kappa-1$) to its maximum value, whereas $\beta_{l1}$ decreases from its maximum value (previously calculated at the zero crossing at step $\kappa-1$) to its minimum value.
    $I_{ZC}^\kappa = [t_{r,ZC}^{\kappa-1}, t_{l,ZC}^\kappa]$ when $\beta_{r1}$ decreases from its maximum value (previously calculated at the zero crossing at step $\kappa-1$) to its minimum value and $\beta_{l1}$ increases from its minimum value (calculated previously at the zero crossing at step $\kappa-1$) to its maximum value.

The determination of a value of $\beta_l$ for a time sample of each interval is sufficient to find the parameters of the change model of $\beta_1$. Using only the values $\beta_r$ and $\beta_l$, it is not possible to determine the angle values at $\beta_1$. Consequently additional information or hypotheses must be included.

For example, during walking, at $t=t_{ZC}$ it can be considered that the angle of the knee $\beta_2$ is close to zero. However, the exact values can be predicted only with difficulty since they depend a great deal on the behaviour parameters of the walking (for example the slope of the walking, the length of the step, the speed, the user, etc.).

It is possible to estimate $\tilde{\beta}_1(t)$ by modelling $\beta_1(t)$ for $t\in[t_{ZC}^{\kappa-1}, t_{ZC}^\kappa]$ by means of a cosine function passing through the estimated values $\beta_1(t_{ZC}^{\kappa-1})$ and $\beta_1(t_{ZC}^\kappa)$. Thus it is not necessary to have a movement sensor to observe $\beta_1$ continuously. Furthermore, since $\beta=\beta_1+\beta_2$, the angle $\tilde{\beta}_2$ is obtained by the following equation:

$$\tilde{\beta}_2(t)=\beta(t)-\tilde{\beta}_1(t) \qquad (19)$$

Consequently it is possible to calculate all the four angles $\{\tilde{\beta}_{r1}(t), \tilde{\beta}_{r2}(t), \tilde{\beta}_{l1}(t), \tilde{\beta}_{l2}(t)\}$.

Finally, the coordinates of the legs are calculated as described previously, where the bearing phase ST is switched between the left and right legs at each placing of the foot on the ground HS.

The coordinates in the reference frame NF linked to the Earth can be calculated, the heading angle $\phi_W^{(l)}$ of the waist (or hips) of the pedestrian being determined from one or all of the magnetometers mounted on the ankles.

Figure 13A:
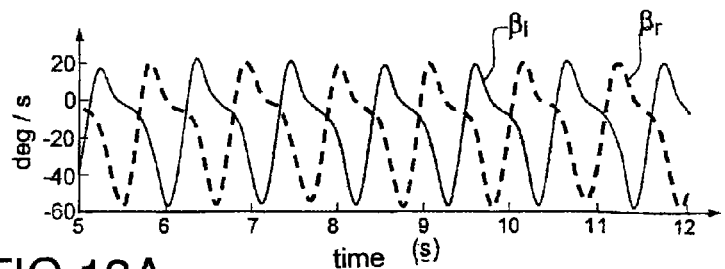
Figure 13B:
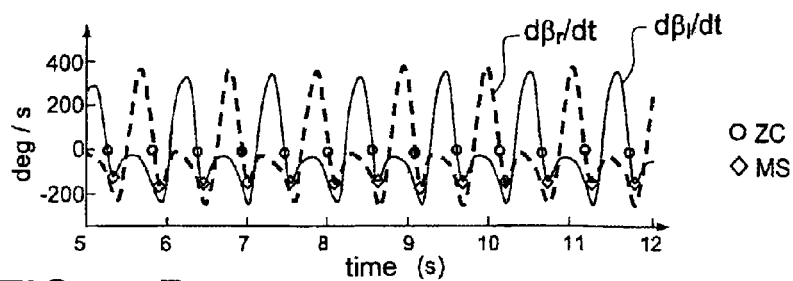
Figure 14A:
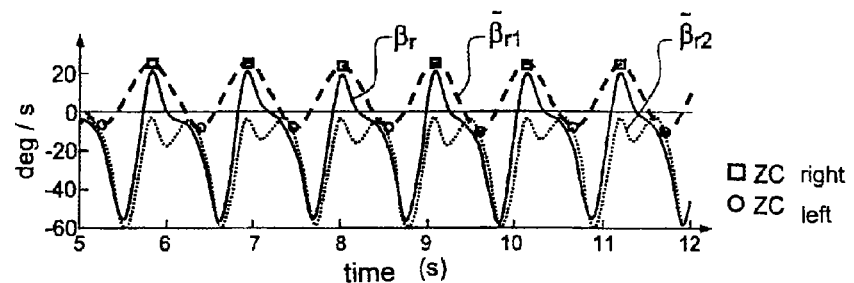
Figure 14B:
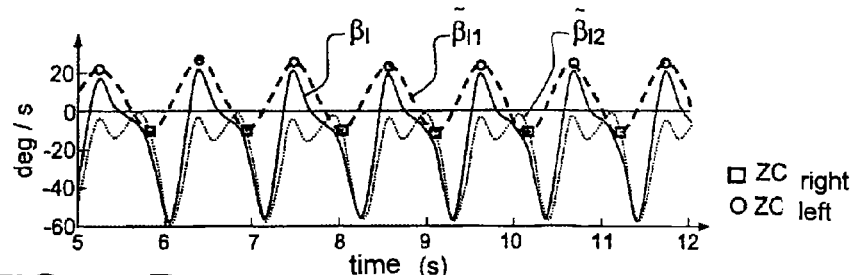

Advantageously, it is possible to use two triaxial magnetometers 3M (or 2M in the plane of the walking) or two triaxial gyrometers 3G (or 1G in the axis orthogonal to the plane of the walking) mounted on each ankle of the pedestrian. Next the following steps are applied:
1) the angles $\beta_r$ and $\beta_l$ are determined as described previously by equations (14) and (15) with a gyrometer or (16), (17) and (18) with a magnetometer. These angles are shown in FIG. 13A. As can be noted, to calculate $\beta(t_0)$, the measurements of the accelerometer in the bearing phase ST (i.e. the measurement of gravity) are necessary for determining the vertical. However $\beta(t_0)$ is initialised without referring to gravity assuming that $\beta(t_0)=0$ at the start of walking when the pedestrian is standing;
2) the angular velocities $d\beta_r/dt$ and $d\beta_l/dt$ are calculated (cf FIG. 13);
3) the detection of a step for detecting the instants HS and ZC is implemented (cf FIG. 13);
4) the angles $\beta_{r1}$ and $\beta_{l1}$ are modelled by cosine functions relying on the occurrences $t_{ZC}^{\kappa-1}$ and $t_{ZC}^\kappa$, and on $\beta(t_{ZC}^{\kappa-1})$ and $\beta(t_{ZC}^\kappa)$ (cf FIGS. 14A and 14B). In this case, $\beta_2(t_{ZC})$ is fixed at $-4°$, and thus $\beta_1(t_{ZC})=\beta(t_{ZC})+4°$;
5) the angles $\tilde{\beta}_{r2}$ and $\tilde{\beta}_{l2}$ are calculated (cf FIGS. 14A and 14B) and the placing of the legs is determined.

The invention claimed is:

1. A method for determining, by a sensor assembly including at least one orientation sensor, values of parameters representing a movement involving at least two limbs of an entity represented in a form of an articulated chain in which each limb is represented by at least one segment and the at least two limbs are connected together by an articulation, the sensor assembly including the at least one orientation sensor being fixed to the entity and configured to measure a parameter representing an orientation of a first segment of the articulated chain, the method comprising:
  receiving an orientation value measured and supplied by the orientation sensor;

estimating a value of at least one first parameter representing a movement of the first segment by processing of the supplied orientation value; and estimating a value of at least one other parameter by executing a time-change model on the basis of a predetermined movement model of the articulated chain, the time-change model including at least one relationship of time dependency between the at least one first parameter and the at least one other parameter representing a movement of another segment of the articulated chain.

2. The determination method according to claim 1, wherein the time-change model further includes a relationship of time dependency, or a relationship of time offset, between movements of at least two distinct limbs of said at least two limbs of the entity, and the at least one other parameter further includes a parameter representing the movement of the another segment of the articulated chain associated with at least part of a limb of said at least two limbs of the entity in the form of the articulated chain other than movement of a limb represented at least by the movement of the first segment.

3. The determination method according to claim 1, wherein the time-change model further includes a relationship of time dependency of orientations of all segments of the at least one segment of the articulated chain relative to that of the first segment.

4. The determination method according to claim 1, wherein said each limb in the articulated chain is represented by two upper or lower limbs of the entity;
wherein each limb is represented by two segments connected together by the articulation, the articulated chain having six degrees of freedom, or
wherein each limb is represented by three segments connected together in pairs by two articulations, the articulated chain having eight degrees of freedom.

5. A non-transitory computer readable storage medium including computer executable instructions stored thereon, which, when executed by a processor, cause the processor to execute a method for determining, by a sensor assembly including at least one orientation sensor, values of parameters representing a movement involving at least two limbs of an entity represented in a form of an articulated chain in which each limb is represented by at least one segment and the at least two limbs are connected together by an articulation, the sensor assembly including the at least one orientation sensor being fixed to the entity and configured to measure a parameter representing an orientation of a first segment of the articulated chain, the method comprising:
receiving an orientation value measured and supplied by the orientation sensor;
estimating, using the processor, a value of at least one first parameter representing a movement of the first segment by processing of the supplied orientation value; and
estimating, using the processor, a value of at least one other parameter by executing a time-change model on the basis of a predetermined movement model of the articulated chain, the time-change model including at least one relationship of time dependency between the at least one first parameter and the at least one other parameter representing a movement of another segment of the articulated chain.

6. A system for determining values of parameters representing a movement involving at least two limbs of an entity represented in a form of an articulated chain in which each limb is represented by at least one segment and the at least two limbs are connected together by an articulation, the system comprising:
at least one orientation sensor configured to measure a parameter representing an orientation of a first segment of the articulated chain, wherein the at least one orientation sensor is further configured to be fixed to a part of the limb of the entity represented by the first segment; and
a processor configured to:
process orientation values measured and supplied by the at least one orientation sensor;
estimate a value of at least one first parameter representing a movement of the first segment using the supplied orientation value; and
estimate a value of at least one other parameter by executing a time-change model on the basis of a predetermined movement model of the articulated chain, the time-change model including at least one relationship of time dependency between the at least one first parameter and the at least one other parameter representing a movement of another segment of the articulated chain.

7. The determination method according to claim 1, wherein the at least one orientation sensor of the sensor assembly fixed to the entity includes a magnetometer having at least one measurement axis and a gyrometer having at least one measurement axis.

8. The determination method according to claim 1, wherein the at least one orientation sensor of the sensor assembly fixed to the entity includes plural orientation sensors, with at least one orientation sensor of said plural orientation sensors per limb of the at least two limbs of the entity.

9. The determination method according to claim 1, wherein the at least one orientation sensor of the sensor assembly fixed to the entity includes an acceleration sensor having at least two measurement axes fixed to a part of a limb of the at least two limbs represented by the movement of the first segment, and further comprising estimating, using the acceleration sensor, cartesian position values of a point linked to the first segment.

10. The determination method according to claim 1, further comprising at least one of:
detecting a placing on ground of a foot of the entity represented by the articulated chain,
estimating an inter-foot distance of at least one foot of the entity represented by the articulated chain, and
detecting movement cycles or particular instances characteristic of the movement cycles of at least one foot of the entity represented by the articulated chain.

11. The determination method according to claim 4, wherein the entity is represented in a form of a living or an artificial being.

* * * * *